(12) United States Patent
Almario Garcia et al.

(10) Patent No.: US 7,566,720 B2
(45) Date of Patent: *Jul. 28, 2009

(54) 2-PYRIDINYL-6,7,8,9-TETRAHYDROPYRIMIDO[1,2-A] PYRIMIDIN-4-ONE AND 7-PYRIDINYL-2,3-DIHYDROIMIDAZO[1,2-A] PYRIMIDIN-5(1H)ONE DERIVATIVES

(75) Inventors: Antonio Almario Garcia, Chatenay Malabry (FR); Thierry Gallet, Palaiseau (FR); Adrien Tak Li, Fontenay Aux Roses (FR); Alistair Lochead, Charenton le Pont (FR); Severine Marguerie, Rennes (FR); Alain Nedelec, Colombes (FR); Mourad Saady, Paris (FR); Philippe Yaiche, Les Lilas (FR)

(73) Assignees: Sanofi-Aventis, Paris (FR); MItsubishi Pharma Corporation, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/841,285

(22) Filed: Aug. 20, 2007

(65) Prior Publication Data

US 2008/0027078 A1 Jan. 31, 2008

Related U.S. Application Data

(63) Continuation of application No. 11/227,007, filed on Sep. 15, 2005, now abandoned, which is a continuation of application No. 10/362,850, filed as application No. PCT/EP01/10726 on Aug. 31, 2001, now Pat. No. 6,974,819.

(30) Foreign Application Priority Data

Sep. 1, 2000 (EP) ................................. 00402410
Sep. 1, 2000 (EP) ................................. 00402412

(51) Int. Cl.
*A61P 25/00* (2006.01)
*A61P 25/28* (2006.01)
*A61P 3/04* (2006.01)
*C07D 471/04* (2006.01)
*C07D 487/04* (2006.01)
*A61K 31/519* (2006.01)

(52) U.S. Cl. .................................. 514/259.5
(58) Field of Classification Search ............... 514/259.5
See application file for complete search history.

(56) References Cited

FOREIGN PATENT DOCUMENTS

WO WO 00/18758 4/2000

OTHER PUBLICATIONS

Bhat, et al., J. Neurochem., 2004, 89, 1313-1317.*
Martinez, et al., Med. Res. Rev., vol. 22, No. 4, 373-384 (2002).*
Buée, et al., Brain Res. Rev., 33 (2000) 95-130.*
Henriksen, et al., Curr. Drug Targets, 2006, 7 (11), 1435+ (Abstract).*
Gould et al., Curr. Drug Targets, Nov. 2006 7(11): 1399-409 (Abstract).*
Harwood, Curr. Mol. Med., Aug. 2003; 3(5): 472-82.*
Zhao, et al., Schizophr. Res., May 2006; 84(1). Epub Apr. 11, 2006 (Abstract).*
Gould, Expert Opin. Ther. Targets, Jun. 2006; 10(3):377+ (Abstract).*
Kwok, et al., Annals of Neurology, vol. 58, No. 6, Dec. 2005, pp. 829-839.*
Nadri, et al., Schizophrenia Research, 71 (2004), 377-382.*
Ciaraldi, et al., Am. J. Physiol. Endocrinol. Metab. 291: E891-E898, 2006.*
Abbosh, P.H., et. al., Multiple Signaling Pathways coverage on Beta-Catenin in Thyroid Cancer, http://www.ncbi.nlm.nih.gov/entrez/query.fcgi?CMD=search&DB-pubmed, 2005.
Alao, J.P., et. al., Histone Deacetylase Inhibitor, Trichostatin A Induces Ubiquitin-Dependent Cyclin DI Degradation in MCF-7 Breast Cancer Cells, Molecular Cancer, vol. 5, No. 8, (2006) pp. 1-11.
Bhat, R.V., et. al., Glycogen Synthase Kinase 3: A Drug Target for CNS Therapies, Journal of Neurochemistry, vol. 89, pp. 1313-1317 (2004).
Chen, G., et. al., Glycogen Synthase Kinase 3B (GSK3B) Mediates 6-Hydroxydopamine-Induced Neuronal Death, The FASEB Journal Express Article 10.1096/fj.04-1551fje. Published online May 7, 2004.
Harwood, A.J., et. al., Neurodevelopment and Mood Stabilizers, Pubmed abstract of Curr. Mol. Med. (2003) vol. 3, No. 5, pp. 472-482.
Kwok, J. B. J., et. al., GSK3B Polymorphisms Alter Transcription and Splicing in Parkinson's Disease, Annals of Neurology, vol. 58, No. 6, (2005) pp. 829-839.
Leclerc, S., et. al., Indirubins Inhibit Glycogen Synthase Kinase-3B and CDK5/P25, Two Protein Kinases Involved in Abnormal Tau Phosphorylation in Alzheimer's Disease, The Journal of Biological Chemistry, vol. 276, No. 1 pp. 251-260 (2001).

(Continued)

*Primary Examiner*—Mark L Berch
*Assistant Examiner*—Cecilia M Jaisle
(74) *Attorney, Agent, or Firm*—Balaram Gupta

(57) ABSTRACT

The invention relates to therapeutic uses of a pyrimidone derivative represented by formula (I) or a salt thereof:

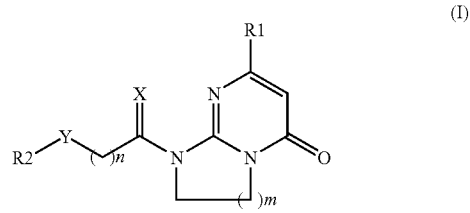

Wherein X, Y, R1, R2, m and n are as defined herein. Specifically, a medicament comprising the said derivative or a salt thereof as an active ingredient is used for preventive and/or therapeutic treatment of a neurodegenerative diseases caused by abnormal activity of GSK3β such as Alzheimer's disease.

5 Claims, No Drawings

OTHER PUBLICATIONS

Luo, H., et. al., Ubiquitin-Dependent Proteolysis of Cyclin D1 Is Associated With Coxsackievirus-Induced Cell Growth Arrest, Journal of Virology, (2003) p. 1-9, vol. 77, No. 1.

Nadri, C., et. al., GSK-3 Parameters in Postmortem Frontal Cortex and Hippocampus of Schizophrenic Patients, Schizophrenic Research, vol. 71, (2004) pp. 377-382.

Alonso, M., et. al., GSK-3 Inhibitors: Discoveries and Developements, Current Medicinal Chemistry, 2004, vol. 11, pp. 755-763.

Eldar-Finkelman, H., et. al., Challenges and Opportunities with Glycogen Synthase Kinase-3 Inhibitors for Insulin Resistance and Type 2 Diabetes Treatment, Expert Opinion Investig Drugs, Sep. 2003;12(9): pp. 1511-1519.

Wagman, A.S., et. al., Discovery and Developement of GSK3 Inhibitors for the Treatment of Type 2 Diabetes, Current Pharmaceutical Design, 2004, vol. 10, pp. 1105-1137.

West, A., et. al., Solid Solutions, Solid State Chemistry and it Applications, Wiley, New York, 1988, pp. 358 & 365.

* cited by examiner

2-PYRIDINYL-6,7,8,9-TETRAHYDRO-PYRIMIDO[1,2-A] PYRIMIDIN-4-ONE AND 7-PYRIDINYL-2,3-DIHYDROIMIDAZO[1,2-A] PYRIMIDIN-5(1H)ONE DERIVATIVES

CROSS REFERENCE TO RELATED APPLICATIONS

This application is a continuation of U.S. application Ser. No. 11/227,007, filed Sep. 15, 2005, now abandoned, which is a continuation of U.S. application Ser. No. 10/362,850, filed Jun. 17, 2003, now U.S. Pat. No. 6,974,819, Issued Dec. 13, 2005, which was the National Stage of International application No. PCT/EP01/10,726, filed Aug. 31, 2001, all of which are incorporated herein by reference in their entirety; which claims the benefit of priority of European Patent Application No. 00/402410.5, filed Sep. 1, 2000 and European Patent Application No. 00/402412.1, filed Sep. 1, 2000.

TECHNICAL FIELD

The present invention relates to compounds that are useful as an active ingredient of a medicament for preventive and/or therapeutic treatment of neurodegenerative diseases caused by abnormal activity of GSK3β.

BACKGROUND ART

GSK3β (glycogen synthase kinase 3β) is a proline directed serine, threonine kinase that plays an important role in the control of metabolism, differentiation and survival. It was initially identified as an enzyme able to phosphorylate and hence inhibit glycogen synthase. It was later recognized that GSK3β was identical to tau protein kinase 1 (TPK1), an enzyme that phosphorylates tau protein in epitopes that are also found to be hyperphosphorylated in Alzheimer's disease and in several tauopathies. Interestingly, protein kinase B (AKT) phosphorylation of GSK3β results in a loss of its kinase activity, and it has been hypothesized that this inhibition may mediate some of the effects of neurotrophic factors. Moreover, phosphorylation by GSK3β of β-catenin, a protein involved in cell survival, results in its degradation by an ubiquitinilation dependent proteasome pathway.

Thus, it appears that inhibition of GSK3β activity may result in neurotrophic activity. Indeed there is evidence that lithium, an uncompetitive inhibitor of GSK3β, enhances neuritogenesis in some models and also increases neuronal survival, through the induction of survival factors such as Bcl-2 and the inhibition of the expression of proapoptotic factors such as P53 and Bax.

Recent studies have demonstrated that β-amyloid increases the GSK3β activity and tau protein phosphorylation. Moreover, this hyperphosphorylation as well as the neurotoxic effects of β-amyloid are blocked by lithium chloride and by a GSK3β antisense mRNA. These observations strongly suggest that GSK3β may be the link between the two major pathological processes in Alzheimer's disease: abnormal APP (Amyloid Precursor Protein) processing and tau protein hyperphosphorylation. Although tau hyperphosphorylation results in a destabilization of the neuronal cytoskeleton, the pathological consequences of abnormal GSK3β activity are, most likely, not only due to a pathological phosphorylation of tau protein because, as mentioned above, an excessive activity of this kinase may affect survival through the modulation of the expression of apoptotic and antiapoptotic factors. Moreover, it has been shown that β-amyloid-induced increase in GSK3β activity results in the phosphorylation and, hence the inhibition of pyruvate dehydrogenase, a pivotal enzyme in energy production and acetylcholine synthesis.

Altogether these experimental observations indicate that GSK3β may find application in the treatment of the neuropathological consequences and the cognitive and attention deficits associated with Alzheimer's disease, as well as other acute and chronic neurodegenerative diseases. These include, in a non-limiting manner, Parkinson's disease, tauopathies (e.g. frontotemporoparietal dementia, corticobasal degeneration, Pick's disease, progressive supranuclear palsy) and other dementia including vascular dementia; acute stroke and others traumatic injuries; cerebrovascular accidents (e.g. age related macular degeneration); brain and spinal cord trauma; peripheral neuropathies; retinopathies and glaucoma. In addition GSK3β may find application in the treatment of other diseases such as: Non-insulin dependent diabetes (such as diabetes type II) and obesity; manic depressive illness; schizophrenia; alopecia; cancers such as breast cancer, non-small cell lung carcinoma, thyroid cancer, T or B-cell leukemia and several virus-induced tumors

DISCLOSURE OF THE INVENTION

An object of the present invention is to provide compounds useful as an active ingredient of a medicament for preventive and/or therapeutic treatment of a disease caused by abnormal GSK3β activity, more particularly of neurodegenerative diseases. More specifically, the object is to provide novel compounds useful as an active ingredient of a medicament that enables prevention and/or treatment of neurodegenerative diseases such as Alzheimer's disease.

Thus, the inventors of the present invention have identified compounds possessing inhibitory activity against GSK3β. As a result, they found that compounds represented by the following formula (I) had the desired activity and were useful as an active ingredient of a medicament for preventive and/or therapeutic treatment of the aforementioned diseases.

The present invention thus provides pyrimidone derivatives represented by formula (I) or salts thereof, solvates thereof or hydrates thereof:

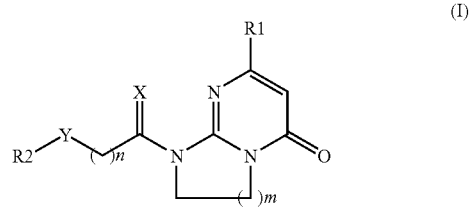

wherein:

X represents hydrogen atoms, a sulfur atom, an oxygen atom or a $C_{1-2}$ alkyl group and a hydrogen atom;

Y represents a bond, an ethenylene group, an ethynylene group, a 1,2-cyclopropylene, an oxygen atom, a sulfur atom, a sulfonyl group, a sulfinyl group, a carbonyl group, a nitrogen atom being optionally substituted by a $C_{1-6}$ alkyl group, a phenyl or a benzyl group; or a methylene group optionally substituted by one or two groups chosen from a $C_{1-6}$ alkyl group, a phenyl group, a hydroxyl group or a $C_{1-4}$ alkoxy group;

R1 represents a 2, 3 or 4-pyridyl group optionally substituted by a $C_{3-6}$ cycloalkyl group a $C_{1-4}$ alkyl group, a $C_{1-4}$ alkoxy group, a benzyl group or a halogen atom;

when Y represents a bond, a 1,2-cyclopropylene, a methylene group optionally substituted or a carbonyl group then R2 represents a $C_{1-6}$ alkyl group, a $C_{3-6}$ cycloalkyl group, a $C_{1-4}$ alkylthio group, a $C_{1-4}$ alkoxy group, a $C_{1-2}$ perhalogenated alkyl group, a $C_{1-3}$ halogenated alkyl group, a 5,6,7,8-tetrahydronaphthyl ring, a naphthyl ring, a phenylthio group, a benzyl group, a phenyl ring, a pyridyl ring, an indole ring, a pyrrole ring, a thiophene ring, a furan ring or an imidazole ring; the benzyl group or the rings being optionally substituted by 1 to 4 substituents selected from a $C_{1-6}$ alkyl group, a methylenedioxy group, a halogen atom, a $C_{1-2}$ perhalogenated alkyl group, a $C_{1-3}$ halogenated alkyl group, a hydroxyl group, a $C_{1-4}$ alkoxy group, a nitro, a cyano, an amino, a $C_{1-5}$ monoalkylamino group, a $C_{2-10}$ dialkylamino group, a $C_{1-6}$ alkylcarbonylamino group, a $C_{6,10}$ arylcarbonylamino group, a $C_{1-4}$ alkylsulfonyl group, $C_{1-4}$ alkylsulfonyloxy group or a phenyl group;

when Y represents an ethenylene group, an ethynylene group, an oxygen atom, a sulfur atom, a sulfonyl group, a sulfinyl group or a nitrogen atom being optionally substituted then R2 represents a $C_{1-6}$ alkyl group, a $C_{3-6}$ cycloalkyl group, a $C_{1-2}$ perhalogenated alkyl group, a $C_{1-3}$ halogenated alkyl group, a naphthyl ring, a 5,6,7,8-tetrahydronaphthyl ring, a benzyl group, a phenyl ring, a pyridyl ring, an indole ring, a pyrrole ring, a thiophene ring, a furan ring or an imidazole ring; the benzyl group or the rings being optionally substituted by 1 to 4 substituents selected from a $C_{1-6}$ alkyl group, a methylenedioxy group, a halogen atom, a $C_{1-2}$ perhalogenated alkyl group, a $C_{1-3}$ halogenated alkyl group, a hydroxyl group, a $C_{1-4}$ alkoxy group, a nitro, a cyano, an amino, a $C_{1-5}$ monoalkylamino group, a $C_{2-10}$ dialkylamino group, a $C_{1-6}$ alkylcarbonylamino group, a $C_{6,10}$ arylcarbonylamino group, a $C_{1-4}$ alkylsulfonyl group, $C_{1-4}$ alkylsulfonyloxy group or a phenyl group;

m represents 1 or 2;

and n represents 0 to 3.

According to another aspect of the present invention, there is provided a medicament comprising as an active ingredient a substance selected from the group consisting of the pyrimidone derivatives represented by formula (I) and the physiologically acceptable salts thereof, and the solvates thereof and the hydrates thereof. As preferred embodiments of the medicament, there are provided the aforementioned medicament which is used for preventive and/or therapeutic treatment of diseases caused by abnormal GSK3β activity, and the aforementioned medicament which is used for preventive and/or therapeutic treatment of neurodegenerative diseases and in addition other diseases such as:

Non-insulin dependent diabetes (such as diabetes type II) and obesity; manic depressive illness; schizophrenia; alopecia; cancers such as breast cancer, non-small cell lung carcinoma, thyroid cancer, T or B-cell leukemia and several virus-induced tumors.

As further preferred embodiments of the present invention, there are provided the aforementioned medicament wherein the diseases are neurodegenerative diseases and are selected from the group consisting of Alzheimer's disease, Parkinson's disease, tauopathies (e.g. frontotemporoparietal dementia, corticobasal degeneration, Pick's disease, progressive supranuclear palsy) and other dementia including vascular dementia; acute stroke and others traumatic injuries; cerebrovascular accidents (e.g. age related macular degeneration); brain and spinal cord trauma; peripheral neuropathies; retinopathies and glaucoma, and the aforementioned medicament in the form of pharmaceutical composition containing the above substance as an active ingredient together with one or more pharmaceutical additives.

The present invention further provides an inhibitor of GSK3β activity comprising as an active ingredient a substance selected from the group consisting of the pyrimidone derivatives of formula (I) and the salts thereof, and the solvates thereof and the hydrates thereof.

According to further aspects of the present invention, there is provided a method for preventive and/or therapeutic treatment of neurodegenerative diseases caused by abnormal GSK3β activity, which comprises the step of administering to a patient a preventively and/or therapeutically effective amount of a substance selected from the group consisting of the pyrimidone derivatives of formula (I) and the physiologically acceptable salts thereof, and the solvates thereof and the hydrates thereof; and a use of a substance selected from the group consisting of the pyrimidone derivatives of formula (I) and the physiologically acceptable salts thereof, and the solvates thereof and the hydrates thereof for the manufacture of the aforementioned medicament.

As used herein, the $C_{1-6}$ alkyl group represents a straight or branched alkyl group having 1 to 6 carbon atoms, for example, methyl group, ethyl group, n-propyl group, isopropyl group, n-butyl group, isobutyl group, sec-butyl group, tert-butyl group, n-pentyl group, isopentyl group, neopentyl group, 1,1-dimethylpropyl group, n-hexyl group, isohexyl group, and the like;

The $C_{3-6}$ cycloalkyl group represents a cyclic alkyl group having from 3 to 6 carbon atoms;

The $C_{1-4}$ alkoxy group represents an alkyloxy group having 1 to 4 carbon atoms for example, methoxy group, ethoxy group, propoxy group, isopropoxy group, butoxy group, isobutoxy group, sec-butoxy group, tert-butoxy group, and the like;

The $C_{1-4}$ alkylthio group represents an alkylthio group having 1 to 4 carbon atoms for example, methylthio group, ethylthio group, propylthio group, isopropylthio group, butylthio group, isobutylthio group, sec-butylthio group, tert-butylthio group, and the like;

The $C_{1-4}$ alkylsulfonyl group represents an alkylsulfonyl group having 1 to 4 carbon atoms for example, methylsulfonyl group, ethylsulfonyl group, propylsulfonyl group, isopropylsulfonyl group, butylsulfonyl group, isobutylsulfonyl group, sec-butylsulfonyl group, tert-butylsulfonyl group, and the like;

The halogen atom represents a fluorine, chlorine, bromine or iodine atom;

The $C_{1-2}$ perhalogenated alkyl group represents an alkyl group wherein all the hydrogen have been substituted by halogen atoms, for example a $CF_3$ or $C_2F_5$;

The $C_{1-3}$ halogenated alkyl group represents an alkyl group wherein at least one hydrogen has not been substituted by a halogen atom;

The $C_{1-5}$ monoalkylamino group represents an amino group substituted by one $C_{1-5}$ alkyl group, for example, methylamino group, ethylamino group, propylamino group, isopropylamino group, butylamino group, isobutylamino group, tert-butylamino group, pentylamino group and isopentylamino group;

The $C_{2-10}$ dialkylamino group represents an amino group substituted by two $C_{1-5}$ alkyl groups, for example, dimethylamino group, ethylmethylamino group, diethylamino group, methylpropylamino group and diisopropylamino group;

The $C_{1-6}$ alkylcarbonylamino group represents an amino group substituted by a $C_{1-6}$ acyl group, for example, formyl group, acetyl group, propionyl group, pivaloyl group, butyryl group, isobutyryl group, pentanoyl group, 3-methylbutyryl group and hexanoyl group;

The $C_{6,10}$ arylcarbonylamino group represents an amino group substituted by a benzoyl group and a naphthoyl group;

The ethenylene, ethynylene and the 1,2-cyclopropylene group represents respectively the following groups:

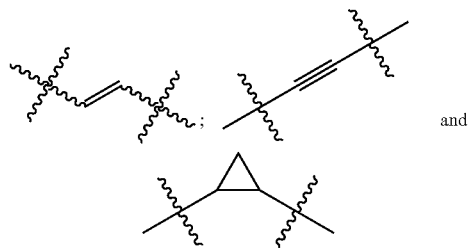

and

The leaving group represents a group which could be easily cleaved and substituted, such a group may be for example a tosyl, a mesyl, a bromide and the like.

The compounds represented by the aforementioned formula (I) may form a salt. Examples of the salt include, when an acidic group exists, salts of alkali metals and alkaline earth metals such as lithium, sodium, potassium, magnesium, and calcium; salts of ammonia and amines such as methylamine, dimethylamine, trimethylamine, dicyclohexylamine, tris(hydroxymethyl)aminomethane, N,N-bis(hydroxyethyl)piperazine, 2-amino-2-methyl-1-propanol, ethanolamine, N-methylglucamine, and L-glucamine; or salts with basic amino acids such as lysine, δ-hydroxylysine, and arginine. The base-addition salts of acidic compounds are prepared by standard procedures well known in the art.

When a basic group exists, examples include salts with mineral acids such as hydrochloric acid, hydrobromic acid, sulfuric acid, nitric acid, phosphoric acid; salts with organic acids such as methanesulfonic acid, benzenesulfonic acid, p-toluenesulfonic acid, acetic acid, propionic acid, tartaric acid, fumaric acid, maleic acid, malic acid, oxalic acid, succinic acid, citric acid, benzoic acid, mandelic acid, cinnamic acid, lactic acid, glycolic acid, glucuronic acid, ascorbic acid, nicotinic acid, and salicylic acid; or salts with acidic amino acids such as aspartic acid, and glutamic acid.

The acid-addition salts of the basic compounds are prepared by standard procedures well know in the art which include, but are not limited thereto, dissolving the free base in an aqueous alcohol solution containing the appropriate acid and isolating the salt by evaporating the solution, or by reacting the free base and an acid in an organic solvent, in which case the salt separates directly, or is precipitated with a second organic solvent, or can be obtained by concentration of the solution. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial properties inherent in the free base are not compromised by side effects ascribable to the anions. Although medicinally acceptable salts of the basic compounds are preferred, all acid-addition salts are within the scope of the present invention.

In addition to the pyrimidinone derivatives represented by the aforementioned formula (I) and salts thereof, their solvates and hydrates also fall within the scope of the present invention. The pyrimidinone derivatives represented by the aforementioned formula (I) may have one or more asymmetric carbon atoms. As for the stereochemistry of such asymmetric carbon atoms, they may independently be in either (R) and (S) configuration, and the pyrimidinone derivative may exist as stereoisomers such as optical isomers, or diastereoisomers. Any stereoisomers in pure form, any mixtures of stereoisomers, racemates and the like fall within the scope of the present invention.

Examples of preferred compounds of the present invention are shown in table 1 hereinafter. However, the scope of the present invention is not limited by these compounds.

Preferred compounds of the present invention represented by formula (I) include also:
(1) Compounds wherein R1 represents a 3- or 4-pyridyl group and more preferably 4-pyridyl group, which may be substituted by a $C_{1-2}$ alkyl group, $C_{1-2}$ alkoxy group or a halogen atom; and/or
(2) Compounds wherein X represents hydrogen atoms, an oxygen atom or a methyl group and a hydrogen atom; and/or
(3) Compounds wherein Y represents a bond, an ethenylene group, an ethynylene group, an oxygen atom, a sulfur atom, a sulfinyl group, a carbonyl group, a methylene group optionally substituted or a nitrogen atom being optionally substituted by one or two benzyl group; and/or
(4) R2 represents a $C_{1-4}$ alkyl group, $C_{1-2}$ alkylthio group, $C_{1-2}$ alkoxy group, a trifluoromethyl group, a $C_{5-6}$ cycloalkyl group, a naphthyl ring, a 5,6,7,8-tetrahydronaphthyl ring, a phenylthio group, a benzyl group, a phenyl ring, a pyridyl ring, an indole ring, a thiophene ring; the rings being optionally substituted by 1 to 4 substituents.

More preferred compounds of the present invention represented by formula (I) include also:
(1) Compounds wherein R1 represents an unsubstituted 4-pyridyl group; and/or
(2) Compounds wherein R2 represents a $C_{1-4}$ alkyl group, $C_{1-2}$ alkylthio group, $C_{1-2}$ alkoxy group, a trifluoromethyl group, a $C_{5-6}$ cycloalkyl group, a naphthyl ring, a 5,6,7,8-tetrahydronaphthyl ring, a phenyl ring, a pyridyl ring, an indole ring, a thiophene ring; the rings being optionally substituted by 1 to 4 substituents; and/or
(3) Compounds wherein X represents hydrogen atoms, an oxygen atom or a methyl group and a hydrogen atom; and/or
(4) Compounds wherein Y represents a bond, a ethenylene, a ethynylene, a sulfur atom, an oxygen atom, a carbonyl group, a sulfinyl group, a methylene group optionally substituted by a $C_{1-4}$ alkyl group and/or a hydroxy group, or a nitrogen atom optionally substituted by one or two benzyl group; and/or
(5) n is 0, 1 or 2.

Particularly preferred compounds of the present invention represented by formula (I) include the compounds of table 1:
1: 9-[2-(H-indol-3-yl)ethyl]-2-pyridin-4-yl-6,7,8,9-tetrahydro-4H-pyrimido[1,2-a]pyrimidin-4-one;
2: 9-(3-phenylpropyl)-2-pyridin-4-yl-6,7,8,9-tetrahydro-4H-pyrimido[1,2-a]pyrimidin-4-one;
3: 9-(2-phenylethyl)-2-pyridin-4-yl-6,7,8,9-tetrahydro-4H-pyrimido[1,2-a]pyrimidin-4-one;
4: 9-[3-(1H-indol-3-yl)propyl]-2-pyridin-4-yl-6,7,8,9-tetrahydro-4H-pyrimido[1,2-a]pyrimidin-4-one;
5: 9-(2-phenoxyethyl)-2-pyridin-4-yl-6,7,8,9-tetrahydro-4H-pyrimido[1,2-a]pyrimidin-4-one;
6: 9-[3-(3,4-methylenedioxyphenyl)propyl]-2-pyridin-4-yl-6,7,8,9-tetrahydro-4H-pyrimido[1,2-a]pyrimidin-4-one;

7: 9-[2-(2-methoxyphenyl)ethyl]-2-pyridin-4-yl-6,7,8,9-tetrahydro-4H-pyrimido[1,2-a]pyrimidin-4-one;
8: 9-[2-(4-fluorophenoxyethyl)]-2-pyridin-4-yl-6,7,8,9-tetrahydro-4H-pyrimido[1,2-a]pyrimidin-4-one;
9: 9-[3-(2-chlorophenyl)propyl]-2-pyridin-4-yl-6,7,8,9-tetrahydro-4H-pyrimido[1,2-a]pyrimidin-4-one;
10: 9-[3-(4-methylpheny)propyl]-2-pyridin-4-yl-6,7,8,9-tetrahydro-4H-pyrimido[1,2-a]pyrimidin-4-one;
11: 9-[3-(4-trifluoromethylphenyl)propyl]-2-pyridin-4-yl-6,7,8,9-tetrahydro-4H-pyrimido[1,2-a]pyrimidin-4-one;
12: 9-(4-phenylbutyl)-2-pyridin-4-yl-6,7,8,9-tetrahydro-4H-pyrimido[1,2-a]pyrimidin-4-one;
13: 9-[3-(2-methylphenyl)propyl]-2-pyridin-4-yl-6,7,8,9-tetrahydro-4H-pyrimido[1,2-a]pyrimidin-4-one;
14: 9-[2-(2,5-dimethoxyphenyl)ethyl]-2-pyridin-4-yl-6,7,8,9-tetrahydro-4H-pyrimido[1,2-a]pyrimidin-4-one;
15: 9-[2-(2-methoxyphenoxy)ethyl]-2-pyridin-4-yl-6,7,8,9-tetrahydro-4H-pyrimido[1,2-a]pyrimidin-4-one;
16: 9-[3-(2-methoxyphenyl)propyl]-2-pyridin-4-yl-6,7,8,9-tetrahydro-4H-pyrimido[1,2-a]pyrimidin-4-one;
17: 9-[2-(4-chlorophenoxy)ethyl]-2-pyridin-4-yl-6,7,8,9-tetrahydro-4H-pyrimido[1,2-a]pyrimidin-4-one;
18: 9-[3-(3-methoxyphenyl)propyl]-2-pyridin-4-yl-6,7,8,9-tetrahydro-4H-pyrimido[1,2-a]pyrimidin-4-one;
19: 9-(2-methoxyphenylmethyl)-2-pyridin-4-yl-6,7,8,9-tetrahydro-4H-pyrimido[1,2-a]pyrimidin-4-one;
20: 9-[2-phenylthioethyl]-2-pyridin-4-yl-6,7,8,9-tetrahydro-4H-pyrimido[1,2-a]pyrimidin-4-one;
21: 9-[3-(3,4-dimethoxyphenyl)propyl]-2-pyridin-4-yl-6,7,8,9-tetrahydro-4H-pyrimido[1,2-a]pyrimidin-4-one;
22: 9-[3-(3,4,5-trimethoxyphenyl)propyl]-2-pyridin-4-yl-6,7,8,9-tetrahydro-4H-pyrimido[1,2-a]pyrimidin-4-one;
23: 9-[2-(phenylsulfonyl)ethyl]-2-pyridin-4-yl-6,7,8,9-tetrahydro-4H-pyrimido[1,2-a]pyrimidin-4-one;
24: 9-[3-(3,4-fluorophenyl)propyl]-2-pyridin-4-yl-6,7,8,9-tetrahydro-4H-pyrimido[1,2-a]pyrimidin-4-one;
25: 9-[3-phenylpropanoyl]-2-pyridin-4-yl-6,7,8,9-tetrahydro-4H-pyrimido[1,2-a]pyrimidin-4-one;
26: 9-[3-(4-fluorophenyl)propyl]-2-pyridin-4-yl-6,7,8,9-tetrahydro-4H-pyrimido[1,2-a]pyrimidin-4-one;
27: 9-[3-(2,5-dimethoxyphenyl)propyl]-2-pyridin-4-yl-6,7,8,9-tetrahydro-4H-pyrimido[1,2-a]pyrimidin-4-one;
28: 9-[3-(2,4-dichlorophenyl)propyl]-2-pyridin-4-yl-6,7,8,9-tetrahydro-4H-pyrimido[1,2-a]pyrimidin-4-one;
29: 9-[3-(3-fluorophenyl)propyl]-2-pyridin-4-yl-6,7,8,9-tetrahydro-4H-pyrimido[1,2-a]pyrimidin-4-one;
30: 9-[3-(4-chlorophenyl)propyl]-2-pyridin-4-yl-6,7,8,9-tetrahydro-4H-pyrimido[1,2-a]pyrimidin-4-one;
31: 9-(3,3-dimethylbutyl)-2-pyridin-4-yl-6,7,8,9-tetrahydro-4H-pyrimido[1,2-a]pyrimidin-4-one;
32: 9-(2-cyclohexylethyl)-2-pyridin-4-yl-6,7,8,9-tetrahydro-4H-pyrimido[1,2-a]pyrimidin-4-one
33: 9-[3-(pyridin-3-yl)propyl]-2-pyridin-4-yl-6,7,8,9-tetrahydro-4H-pyrimido[1,2-a]pyrimidin-4-one;
34: 9-[2-(4-methylsulfonyloxyphenyl)ethyl]-2-pyridin-4-yl-6,7,8,9-tetrahydro-4H-pyrimido[1,2-a]pyrimidin-4-one;
35: 9-(3-methylbutyl)-2-pyridin-4-yl-6,7,8,9-tetrahydro-4H-pyrimido[1,2-a]pyrimidin-4-one;
36: 9-(3,3-diphenylpropyl)-2-pyridin-4-yl-6,7,8,9-tetrahydro-4H-pyrimido[1,2-a]pyrimidin-4-one;
37: 9-[4-(4-methoxyphenyl)butyl]-2-pyridin-4-yl-6,7,8,9-tetrahydro-4H-pyrimido[1,2-a]pyrimidin-4-one;
38: 9-[4-(4-nitrophenyl)butyl]-2-pyridin-4-yl-6,7,8,9-tetrahydro-4H-pyrimido[1,2-a]pyrimidin-4-one;
39: 9-[3-(2-fluorophenyl)propyl]-2-pyridin-4-yl-6,7,8,9-tetrahydro-4H-pyrimido[1,2-a]pyrimidin-4-one;
40: 9-(3-phenylprop-2-ynyl)-2-pyridin-4-yl-6,7,8,9-tetrahydro-4H-pyrimido[1,2-a]pyrimidin-4-one;
41: 9-(3-phenylbutyl)-2-pyridin-4-yl-6,7,8,9-tetrahydro-4H-pyrimido[1,2-a]pyrimidin-4-one;
42: 9-[2-(2-chloro-4-fluorophenyl)ethyl]-2-pyridin-4-yl-6,7,8,9-tetrahydro-4H-pyrimido[1,2-a]pyrimidin-4-one;
43: 9-(2-phenyl-2-oxo-ethyl)-2-pyridin-4-yl-6,7,8,9-tetrahydro-4H-pyrimido[1,2-a]pyrimidin-4-one;
44: 9-(3-benzyloxypropyl)-2-pyridin-4-yl-6,7,8,9-tetrahydro-4H-pyrimido[1,2-a]pyrimidin-4-one;
45: 9-(3-methylthioethyl)-2-pyridin-4-yl-6,7,8,9-tetrahydro-4H-pyrimido[1,2-a]pyrimidin-4-one;
46: 9-[2-(1-naphthyl)ethyl]-2-pyridin-4-yl-6,7,8,9-tetrahydro-4H-pyrimido[1,2-a]pyrimidin-4-one;
47: 9-[2-(thiophen-2-yl)ethyl]-2-pyridin-4-yl-6,7,8,9-tetrahydro-4H-pyrimido[1,2-a]pyrimidin-4-one;
48: 9-[2-(3-trifluoromethylphenyl)ethyl]-2-pyridin-4-yl-6,7,8,9-tetrahydro-4H-pyrimido[1,2-a]pyrimidin-4-one;
49: 9-[(2-(thiophen-3-yl)ethyl]-2-pyridin-4-yl-6,7,8,9-tetrahydro-4H-pyrimido[1,2-a]pyrimidin-4-one;
50: 9-[2-(2-bromophenyl)ethyl]-2-pyridin-4-yl-6,7,8,9-tetrahydro-4H-pyrimido[1,2-a]pyrimidin-4-one;
51: 9-(4-cyclohexylbutyl)-2-pyridin-4-yl-6,7,8,9-tetrahydro-4H-pyrimido[1,2-a]pyrimidin-4-one
52: 9-[2-(3-bromophenyl)ethyl]-2-pyridin-4-yl-6,7,8,9-tetrahydro-4H-pyrimido[1,2-a]pyrimidin-4-one;
53: 9-[2-(4-tert-butylphenyl)ethyl]-2-pyridin-4-yl-6,7,8,9-tetrahydro-4H-pyrimido[1,2-a]pyrimidin-4-one;
54: 9-[2-(2,4,6-trimethylphenyl)ethyl]-2-pyridin-4-yl-6,7,8,9-tetrahydro-4H-pyrimido[1,2-a]pyrimidin-4-one;
55: 9-[2-(4-ethoxyphenyl)ethyl]-2-pyridin-4-yl-6,7,8,9-tetrahydro-4H-pyrimido[1,2-a]pyrimidin-4-one;
56: 9-[2-(2-chloro-6-fluorophenyl)ethyl]-2-pyridin-4-yl-6,7,8,9-tetrahydro-4H-pyrimido[1,2-a]pyrimidin-4-one;
57: 9-[2-(3-chlorophenyl)ethyl]-2-pyridin-4-yl-6,7,8,9-tetrahydro-4H-pyrimido[1,2-a]pyrimidin-4-one;
58: 9-[2-(3-methylphenyl)ethyl]-2-pyridin-4-yl-6,7,8,9-tetrahydro-4H-pyrimido[1,2-a]pyrimidin-4-one;
59: 9-(3-methoxybutyl)-2-pyridin-4-yl-6,7,8,9-tetrahydro-4H-pyrimido[1,2-a]pyrimidin-4-one;
60: 9-(3-cyclohexylpropyl)-2-pyridin-4-yl-6,7,8,9-tetrahydro-4H-pyrimido[1,2-a]pyrimidin-4-one;
61: 9-[3-[di(phenylmethyl)amino]propyl]-2-pyridin-4-yl-6,7,8,9-tetrahydro-4H-pyrimido[1,2-a]pyrimidin-4-one;
62: 9-(2-phenyl-cyclopropylmethyl)-2-pyridin-4-yl-6,7,8,9-tetrahydro-4H-pyrimido[1,2-a]pyrimidin-4-one;
63: 9-(3-phenylprop-2-enyl)-2-pyridin-4-yl-6,7,8,9-tetrahydro-4H-pyrimido[1,2-a]pyrimidin-4-one;
64: 9-(2-phenyl-2-hydroxypropyl)-2-pyridin-4-yl-6,7,8,9-tetrahydro-4H-pyrimido[1,2-a]pyrimidin-4-one;
65: 9-[3-(4-fluorophenyl)-3-oxo-propyl]-2-pyridin-4-yl-6,7,8,9-tetrahydro-4H-pyrimido[1,2-a]pyrimidin-4-one;
66: 9-(4,4,4-trifluorobutyl)-2-pyridin-4-yl-6,7,8,9-tetrahydro-4H-pyrimido[1,2-a]pyrimidin-4-one;
67: 9-[3-phenyl-3-oxo-propyl]-2-pyridin-4-yl-6,7,8,9-tetrahydro-4H-pyrimido[1,2-a]pyrimidin-4-one;
68: 9-[3-phenyl-3-hydroxypropyl]-2-pyridin-4-yl-6,7,8,9-tetrahydro-4H-pyrimido[1,2-a]pyrimidin-4-one;
69: 9-[3,3,3-trifluoro-2-hydroxypropyl]-2-pyridin-4-yl-6,7,8,9-tetrahydro-4H-pyrimido[1,2-a]pyrimidin-4-one
70: (R)-9-[2-phenyl-2-hydroxyethyl]-2-pyridin-4-yl-6,7,8,9-tetrahydro-4H-pyrimido[1,2-a]pyrimidin-4-one
71: (S)-9-[2-phenyl-2-hydroxyethyl]-2-pyridin-4-yl-6,7,8,9-tetrahydro-4H-pyrimido[1,2-a]pyrimidin-4-one
72: 9-[3-(4-fluorophenyl)-3-hydroxypropyl]-2-pyridin-4-yl-6,7,8,9-tetrahydro-4H-pyrimido[1,2-a]pyrimidin-4-one 73: 9-[1-methyl-2-oxo-2-phenyl-ethyl]-2-pyridin-4-yl-6,7,8,9-tetrahydro-4H-pyrimido[1,2-a]pyrimidin-4-one
74: 9-[1-methyl-2-hydroxy-2-phenyl-ethyl]-2-pyridin-4-yl-6,7,8,9-tetrahydro-4H-pyrimido[1,2-a]pyrimidin-4-one
75: 9-[2-(4-methylphenyl)-2-oxo-ethyl]-2-pyridin-4-yl-6,7,8,9-tetrahydro-4H-pyrimido[1,2-a]pyrimidin-4-one;
76: 9-[2-(4-chlorophenyl)-2-oxo-ethyl]-2-pyridin-4-yl-6,7,8,9-tetrahydro-4H-pyrimido[1,2-a]pyrimidin-4-one;
77: 9-[2-(4-fluorophenyl)-2-oxo-ethyl]-2-pyridin-4-yl-6,7,8,9-tetrahydro-4H-pyrimido[1,2-a]pyrimidin-4-one;
78: 9-[2-(4-phenylphenyl)-2-oxo-ethyl]-2-pyridin-4-yl-6,7,8,9-tetrahydro-4H-pyrimido[1,2-a]pyrimidin-4-one;
79: 9-[2-(3-methoxyphenyl)-2-oxo-ethyl]-2-pyridin-4-yl-6,7,8,9-tetrahydro-4H-pyrimido[1,2-a]pyrimidin-4-one;
80: 9-[2-(2-naphthyl)-2-oxo-ethyl]-2-pyridin-4-yl-6,7,8,9-tetrahydro-4H-pyrimido[1,2-a]pyrimidin-4-one;
81: 9-[2-(5,5,8,8-tetramethyl-5,6,7,8-tetrahydronaphth-2-yl)-2-oxo-ethyl]-2-pyridin-4-yl-6,7,8,9-tetrahydro-4H-pyrimido[1,2-a]pyrimidin-4-one;
82: 9-[2-(3-methoxy-4,5-methylendioxyphenyl)-2-oxo-1-methylethyl]-2-pyridin-4-yl-6,7,8,9-tetrahydro-4H-pyrimido[1,2-a]pyrimidin-4-one;
83: 9-[2-(4-methylphenyl)-2-hydroxy-ethyl]-2-pyridin-4-yl-6,7,8,9-tetrahydro-4H-pyrimido[1,2-a]pyrimidin-4-one;
84: 9-[2-(1,1,4,4-tetramethyl-1,2,3,4-tetrahydronaphth-6-yl)-2-hydroxy-ethyl]-2-pyridin-4-yl-6,7,8,9-tetrahydro-4H-pyrimido[1,2-a]pyrimidin-4-one;
85: 9-[2-(phenylamino)-2-oxo-ethyl]-2-pyridin-4-yl-6,7,8,9-tetrahydro-4H-pyrimido[1,2-a]pyrimidin-4-one;
86: 9-[2-(3-chlorophenyl)-2-oxo-ethyl]-2-pyridin-4-yl-6,7,8,9-tetrahydro-4H-pyrimido[1,2-a]pyrimidin-4-one;
87: 9-[2-(3-chlorophenyl)-2-hydroxy-ethyl]-2-pyridin-4-yl-6,7,8,9-tetrahydro-4H-pyrimido[1,2-a]pyrimidin-4-one;
88: 9-[2-(3-fluorophenyl)-2-oxo-ethyl]-2-pyridin-4-yl-6,7,8,9-tetrahydro-4H-pyrimido[1,2-a]pyrimidin-4-one;
89: 9-[2-(3-fluorophenyl)-2-hydroxy-ethyl]-2-pyridin-4-yl-6,7,8,9-tetrahydro-4H-pyrimido[1,2-a]pyrimidin-4-one;

And the compounds of table 2:
1: 1-[2-(1H-Indol-3-yl)ethyl]-7-pyridin-4-yl-2,3-dihydroimidazo[1,2-a]pyrimidin-5(1H-one,
2: 1-[3-(phenyl)propyl]-7-pyridin-4-yl-2,3-dihydroimidazo[1,2-a]pyrimidin-5(1H)-one,
3: 1-[3-(1H-indol-3-yl)propyl]-7-pyridin-4-yl-2,3-dihydroimidazo[1,2-a]pyrimidin-5(1H)-one,
4: 1-[2-(phenyl)ethyl]-7-pyridin-4-yl-2,3-dihydroimidazo[1,2-a]pyrimidin-5(1H)-one,
5: 1-[3-(2-methylphenyl)propyl]-7-pyridin-4-yl-2,3-dihydroimidazo[1,2-a]pyrimidin-5(1H)-one,
6: 1-[3-(2-methoxyphenyl)propyl]-7-pyridin-4-yl-2,3-dihydroimidazo[1,2-a]pyrimidin-5(1H)-one,
7: 1-(4-phenylbutyl)-7-pyridin-4-yl-2,3-dihydroimidazo[1,2-a]pyrimidin-5(1H)-one,
8: 1-[3-(2-chlorophenyl)propyl]-7-pyridin-4-yl-2,3-dihydroimidazo[1,2-a]pyrimidin-5(1H)-one,
9: 1-[3-(2,5-dimethoxyphenyl)propyl]-7-pyridin-4-yl-2,3-dihydroimidazo[1,2-a]pyrimidin-5(1H)-one,
10 :1-[3-(4-methylphenyl)propyl]-7-pyridin-4-yl-2,3-dihydroimidazo[1,2-a]pyrimidin-5(1H)-one,
11: 1-[3-(3-methoxyphenyl)propyl]-7-pyridin-4-yl-2,3-dihydroimidazo[1,2-a]pyrimidin-5(1H)-one,
12: 1-[3-(3,4,5-trimethoxyphenyl)propyl]-7-pyridin-4-yl-2,3-dihydroimidazo[1,2-a]pyrimidin-5(1H)-one,
13: 1-[2-(4-fluorophenoxy)ethyl]-7-pyridin-4-yl-2,3-dihydroimidazo[1,2-a]pyrimidin-5(1H)-one,
14: 1-[2-(4-chlorophenoxy)ethyl]-7-pyridin-4-yl-2,3-dihydroimidazo[1,2-a]pyrimidin-5(1H)-one,
15: 1-[3-(2,4-dichlorophenyl)propyl]-7-pyridin-4-yl-2,3-dihydroimidazo[1,2-a]pyrimidin-5(1H)-one,
16: 1-[2-(phenylthio)ethyl]-7-pyridin-4-yl-2,3-dihydroimidazo[1,2-a]pyrimidin-5(1-one,
17: 1-(3-phenylpropanoyl)-7-pyridin-4-yl-2,3-dihydroimidazo[1,2-a]pyrimidin-5(1H-one,
18: 1-[3-(4-fluorophenyl)propyl]-7-pyridin-4-yl-2,3-dihydroimidazo[1,2-a]pyrimidin-5(1H)-one,
19: 1-[3-(3,4-difluorophenyl)propyl]-7-pyridin-4-yl-2,3-dihydroimidazo[1,2-a]pyrimidin-5(1H)-one,
20: 1-(2-cyclohexylethyl)-7-pyridin-4-yl-2,3-dihydroimidazo[1,2-a]pyrimidin-5(1H)-one,
21: 1-(3,3-dimethylbutyl)-7-pyridin-4-yl-2,3-dihydroimidazo[1,2-a]pyrimidin-5(1H)-one.
22: 1-(2-phenyl-2-oxo-ethyl)-7-pyridin-4-yl-2,3-dihydroimidazo[1,2-a]pyrimidin-5(1H)-one, and
23: (S)-1-(4,4,4-trifluoro-3-hydroxybutyl)-7-pyridin-4-yl-2,3-dihydroimidazo[1,2-a]pyrimidin-5(1H)-one.
24: 1-(4,4,4-trifluoro-but-2-en-1-yl)-7-pyridin-4-yl-2,3-dihydroimidazo[1,2-a]pyrimidin-5(1H)-one,
25: 1-[3-(4-trifluoromethylphenyl)propyl]-7-pyridin-4-yl-2,3-dihydroimidazo[1,2-a]pyrimidin-5(1H)-one,
26: (R)-1-(4,4,4-trifluoro-3-hydroxybutyl)-7-pyridin-4-yl-2,3-dihydroimidazo[1,2-a]pyrimidin-5(1H)-one,
27: 1-[3-(2-fluorophenyl)propyl]-7-pyridin-4-yl-2,3-dihydroimidazo[1,2-a]pyrimidin-5(1H)-one,
28: 1-[2-(2,5-dimethoxy-phenyl)ethyl]-7-pyridin-4-yl-2,3-dihydroimidazo[1,2-a]pyrimidin-5(1H)-one,
29: 1-[2-(phenylsulfonyl)ethyl]-7-pyridin-4-yl-2,3-dihydroimidazo[1,2-a]pyrimidin-5(1H)-one,
30: 1-(4,4,4-trifluorobutyl)-7-pyridin-4-yl-2,3-dihydroimidazo[1,2-a]pyrimidin-5(1-one,
31: 1-[3-(pyridin-3-yl)propyl]-7-pyridin-4-yl-2,3-dihydroimidazo[1,2-a]pyrimidin-5(1H-one,
32: 1-[2-(2-methoxy)ethyl]-7-pyridin-4-yl-2,3-dihydroimidazo[1,2-a]pyrimidin-5(1H)-one,
33: 1-[2-(4-chloro-phenyl)-2-oxo-ethyl]-7-pyridin-4-yl-2,3-dihydroimidazo[1,2-a]pyrimidin-5(1H)-one,
34: 1-[2-(naphth-2-yl)-2-oxo-ethyl]-7-pyridin-4-yl-2,3-dihydroimidazo[1,2-a]pyrimidin-5(1H)-one,
35: 1-[2-(3-methoxy-4,5-methylendioxy-phenyl)-2-oxo-1-methyl-ethyl]-7-pyridin-4-yl-2,3-dihydroimidazo[1,2-a]pyrimidin-5(1H)-one,
36: 1-[2-(4-phenyl-phenyl)-2-oxo-ethyl]-7-pyridin-4-yl-2,3-dihydroimidazo[1,2-a]pyrimidin-5(1H)-one,
37: 1-[2-(4-methylphenyl)2-oxo-ethyl]-7-pyridin-4-yl-2,3-dihydroimidazo[1,2-a]pyrimidin-5(1H)-one,
38: 1-[2-(5,5,8,8-tetramethyl-5,6,7,8-tetrahydronaphth-2-yl)2-oxo-ethyl]-7-pyridin-4-yl-2,3-dihydroimidazo[1,2-a]pyrimidin-5(1H)-one,
39: 1-[2-(4-fluorophenyl)-2-oxo-ethyl]-7-pyridin-4-yl-2,3-dihydroimidazo[1,2-a]pyrimidin-5(1H)-one,
40: 1-[2-(3-methoxyphenyl)-2-oxo-ethyl]-7-pyridin-4-yl-2,3-dihydroimidazo[1,2-a]pyrimidin-5(1H)-one.

As a further object, the present invention concerns also methods for preparing the pyrimidin-4-one compounds represented by the aforementioned formula (I). These compounds can be prepared, for example, according to methods explained below.

Preparation Method

2-[1,2-a]pyrimidin-4-one compounds represented by the aforementioned formula (I) may be prepared according to scheme 1.

Scheme 1

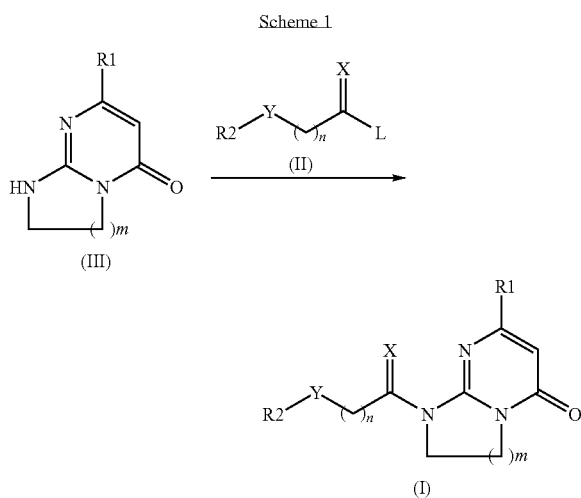

(In the above scheme the definition of R1, R2, X, Y and n are the same as those already described for compound of formula (I)).

The [1,2-a]pyrimidin-4-one derivative represented by the above formula (III), wherein R1 is as defined for compound of formula (I), is allowed to react with a base such as sodium hydride, sodium carbonate or potassium carbonate, in a solvent such as N,N-dimethylformamide, N-methylpyrrolidine, N,N-dimethylacetamide or chloroform, at a suitable temperature ranging from 0 to 130° C. under ordinary air, and then with a compound of formula (II), wherein R2, Y and n are as defined for compound of formula (I) and L represents a leaving group, to obtain the compound of the aforementioned formula (I).

Preferably when X represents hydrogen atoms, L represents a bromide or mesyl group and the reaction is carried out with sodium hydride in N,N-dimethylformamide at a suitable temperature ranging from 70 to 130° C.

Preferably when X represents oxygen atom, L represents a chloride and the reaction is carried out with sodium hydride in chloroform at a suitable temperature ranging from 0 to 70° C.

Compound of formula (II) is commercially available or may be synthesized according to well-known methods of one skilled in the art.

The compound of formula (III) may be prepared according to the method defined in scheme 2.

Scheme 2

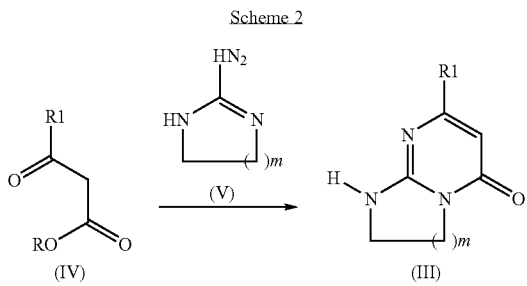

(In the above scheme the definition of R1 is the same as already described.) According to this method, the 3-ketoester of formula (IV) is allowed to react with a compound 2 of formula (V). The reaction may be carried out in an alcoholic solvent such as ethanol, propanol or isopropanol, in presence of a base such as sodium hydride, sodium carbonate or potassium carbonate, at a suitable temperature ranging from 25°-100° C. under ordinary air.

Compound of formula (IV) is commercially available or may be synthesized according to well-known methods of one skilled in the art.

For example compounds of formula (IV), wherein R1 represent a pyridyl group optionally substituted by a $C_{1-4}$ alkyl group, $C_{1-4}$ alkoxy group or a halogen atom, can be prepared by reacting a nicotinic acid optionally substituted by a $C_{1-4}$ alkyl group, $C_{1-4}$ alkoxy group or an halogen, with a malonic acid monoester. The reaction can be carried out using methods well known to one skilled in the art, such as for example in presence of a coupling agent such as 1,1'-carbonylbis-1H-imidazole in a solvent such as tetrahydrofuran at a temperature ranging from 20 to 70° C.

Compound of formula (V) may be synthesized according to the method described by Smith and Christensen (J. Org. Chem. 1955, 20, 829).

Alternatively and when Y represents an oxygen atom, X represents hydrogen atoms and R2 represents an aryl or heteroaryl group, compounds of the aforementioned formula (I) may be prepared according to scheme 3.

Scheme 3

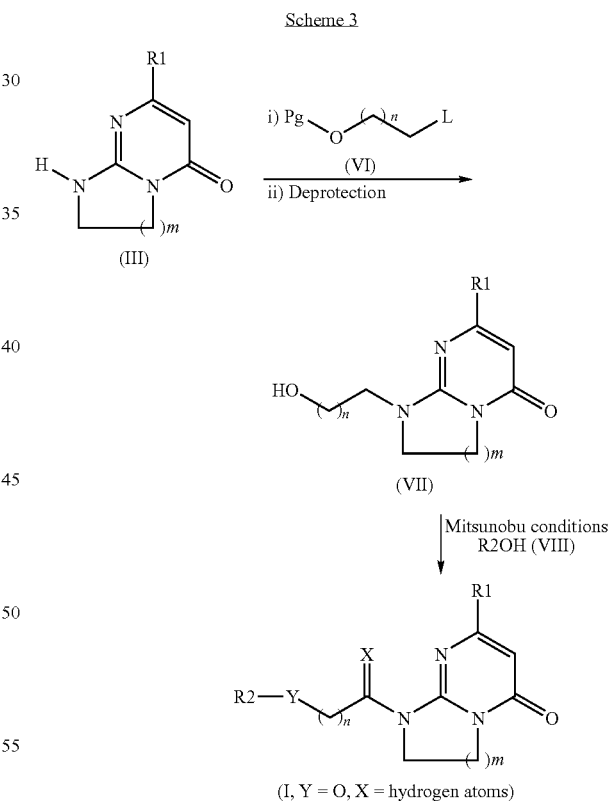

(In the above scheme the definition of R1 is the same as already described.)

According to this method, compounds of formula (III), are allowed to react with a base such as sodium hydride or potassium carbonate in a solvent such as N,N-dimethylformamide at a suitable temperature ranging from 70° to 130° C. under ordinary air, then followed by addition compounds of formula (VI), wherein Pg represents a protecting group, preferably a tetrahydropyran, and L represents a leaving group, preferably a bromide. The deprotection is then carried out using methods well known to one skilled in the art, such as for example when the protecting group is a tetrahydropyran group, the deprotection is then carried out in presence of ammonium chloride in a solvent such as methanol at a temperature ranging from 20° to 70° C. to give compound of formula (VII). Compounds of formula (I), as defined hereinabove, can then be prepared by reacting the compound of formula (VII) with a compound of formula (VIII) using methods well known to one skilled in the art, such as for example in presence of triphenylphosphine and diethylazodicarboxylate as coupling agent in a solvent such tetrahydrofuran at room temperature.

Compounds of formula (VI) and (VIII) are commercially available or may be synthesized according to well-known methods of one skilled in the art.

In the above reactions, protection or deprotection of a functional group may sometimes be necessary. A suitable protecting group Pg can be chosen depending on the type of a functional group, and a method described in the literature may be applied. Examples of protecting groups, of protection and deprotection methods are given for example in *Protective groups in Organic Synthesis* Greene et al., 2nd Ed. (John Wiley & Sons, Inc., New York).

The compounds of the present invention have inhibitory activity against GSK3β. Accordingly, the compounds of the present invention are useful as an active ingredient for the preparation of a medicament, which enables preventive and/or therapeutic treatment of a disease caused by abnormal GSK3β activity and more particularly of neurodegenerative diseases such as Alzheimer's disease. In addition, the compounds of the present invention are also useful as an active ingredient for the preparation of a medicament for preventive and/or therapeutic treatment of neurodegenerative diseases such as Parkinson's disease, tauopathies (e.g. frontotemporoparietal dementia, corticobasal degeneration, Pick's disease, progressive supranuclear palsy) and other dementia including vascular dementia; acute stroke and others traumatic injuries; cerebrovascular accidents (e.g. age related macular degeneration); brain and spinal cord trauma; peripheral neuropathies; retinopathies and glaucoma; and other diseases such as non-insulin dependent diabetes (such as diabetes type II) and obesity; manic depressive illness; schizophrenia; alopecia; cancers such as breast cancer, non-small cell lung carcinoma, thyroid cancer, T or B-cell leukemia and several virus-induced tumors.

The present invention further relates to a method for treating neurodegenerative diseases caused by abnormal activity of GSK3β and of the aforementioned diseases which comprises administering to a mammalian organism in need thereof an effective amount of a compound of the formula (I).

As the active ingredient of the medicament of the present invention, a substance may be used which is selected from the group consisting of the compound represented by the aforementioned formula (I) and pharmacologically acceptable salts thereof, and solvates thereof and hydrates thereof. The substance, per se, may be administered as the medicament of the present invention, however, it is desirable to administer the medicament in a form of a pharmaceutical composition which comprises the aforementioned substance as an active ingredient and one or more pharmaceutical additives. As the active ingredient of the medicament of the present invention, two or more of the aforementioned substances may be used in combination. The above pharmaceutical composition may be supplemented with an active ingredient of another medicament for the treatment of the above mentioned diseases. The type of pharmaceutical composition is not particularly limited, and the composition may be provided as any formulation for oral or parenteral administration. For example, the pharmaceutical composition may be formulated, for example, in the form of pharmaceutical compositions for oral administration such as granules, fine granules, powders, hard capsules, soft capsules, syrups, emulsions, suspensions, solutions and the like, or in the form of pharmaceutical compositions for parenteral administrations such as injections for intravenous, intramuscular, or subcutaneous administration, drip infusions, transdermal preparations, transmucosal preparations, nasal drops, inhalants, suppositories and the like. Injections or drip infusions may be prepared as powdery preparations such as in the form of lyophilized preparations, and may be used by dissolving just before use in an appropriate aqueous medium such as physiological saline. Sustained-release preparations such as those coated with a polymer may be directly administered intracerebrally.

Types of pharmaceutical additives used for the manufacture of the pharmaceutical composition, content ratios of the pharmaceutical additives relative to the active ingredient, and methods for preparing the pharmaceutical composition may be appropriately chosen by those skilled in the art. Inorganic or organic substances, or solid or liquid substances may be used as pharmaceutical additives. Generally, the pharmaceutical additives may be incorporated in a ratio ranging from 1% by weight to 90% by weight based on the weight of an active ingredient.

Examples of excipients used for the preparation of solid pharmaceutical compositions include, for example, lactose, sucrose, starch, talc, cellulose, dextrin, kaolin, calcium carbonate and the like. For the preparation of liquid compositions for oral administration, a conventional inert diluent such as water or a vegetable oil may be used. The liquid composition may contain, in addition to the inert diluent, auxiliaries such as moistening agents, suspension aids, sweeteners, aromatics, colorants, and preservatives. The liquid composition may be filled in capsules made of an absorbable material such as gelatin. Examples of solvents or suspension mediums used for the preparation of compositions for parenteral administration, e.g. injections, suppositories, include water, propylene glycol, polyethylene glycol, benzyl alcohol, ethyl oleate, lecithin and the like. Examples of base materials used for suppositories include, for example, cacao butter, emulsified cacao butter, lauric lipid, witepsol.

The dose and frequency of administration of the medicament of the present invention are not particularly limited, and they may be appropriately chosen depending on conditions such as a purpose of preventive and/or therapeutic treatment, a type of a disease, the body weight or age of a patient, severity of a disease and the like. Generally, a daily dose for oral administration to an adult may be 0.01 to 1,000 mg (the weight of an active ingredient), and the dose may be administered once a day or several times a day as divided portions, or once in several days. When the medicament is used as an injection, administrations may preferably be performed continuously or intermittently in a daily dose of 0.001 to 100 mg (the weight of an active ingredient) to an adult.

CHEMICAL EXAMPLES

The present invention will be explained more specifically with reference to the following general examples, however, the scope of the present invention is not limited to these examples.

Example 1

Compound N° 7 of Table 1

9-[2-(2-Methoxyphenyl)ethyl]-2-pyridin-4-yl-6,7,8, 9-tetrahydro-4H-pyrimido[1,2-a]pyrimidin-4-one (Z)-but-2-enedioate (1:1)

1.1. 2-Pyridin-4-yl-6,7,8,9-tetrahydro-4H-pyrimido [1,2-a]pyrimidin-4-one

A mixture of 8.98 g (46.5 mmol) of ethyl 3-(4-pyridyl)-3-oxopropionate and 8.0 g (46.5 mmol) of 2-amino tetrahydro-pyrimidine dihydrochloride (prepared according to J. Org. Chem. 1955, 20, 829.) and 19.3 g (139.5 mmol) of potassium carbonate in 60 ml of ethanol was heated at reflux temperature during 18 h.

The cooled solution was evaporated to remove solvent and the residue was treated with water and extracted with dichloromethane. The extracts were dried and evaporated to give 8.0 g (75%) of product as a white powder. Mp: 219° C.

1.2. 9-[2-(2-Methoxyphenyl)ethyl]-2-pyridin-4-yl-6, 7,8,9-tetrahydro-4H-pyrimido[1,2-a]pyrimidin-4-one (Z)-but-2-enedioate (1:1)

A suspension of 0.25 g (1.09 mmol) of 2-pyridin-4-yl-6,7, 8,9-tetrahydro-4H-pyrimido[1,2-a]pyrimidin-4-one in 3 ml of anhydrous dimethylformamide was treated with 57 mg (1.42 mmol) of sodium hydride (60% suspension in mineral oil) and the resulting mixture was heated at 70° C. for 30 min. 0.327 g (1.42 mmol) of 1-[2-(methylsulfonyloxy)ethyl]-2-methoxybenzene (prepared according to J. Med. Chem. 1983, 26(1), 42) was added and the reaction mixture was heated at 130° C. during 1 h. The cooled solution was treated with water and extracted with ethyl acetate. The organic phase was dried and evaporated to give crude product, which was purified by silica gel chromatography, eluting with dichloromethane/methanol in the proportions 100/0 to 95/5. The 0.338 g of pure product obtained in the form of free base was dissolved in hot ethanol and treated with 1 equivalent of (Z)-but-2-enedioïc acid. The cooled solution was filtered to afford 0.325 g (62%) of white solid. Mp: 157-160° C.

Example 2

Compound N° 4 of Table 1

9-[3-(1H-Indol-3-yl)propyl]-2-pyridin-4-yl-6,7,8,9-tetrahydro-4H-pyrimido[1,2-a]pyrimidin-4-one 2.1. 3-(1H-Indol-3-yl)propanol (J. Med. Chem. (1995), 38(11), 1998)

To a suspension of 4.8 g (126.8 mmol) of lithium aluminum hydride in 240 ml of diethylether at 0° C. was added dropwise 10 g (52.8 mmol) of 3-(1H-indol-3-yl)propanoic acid dissolved in 430 ml of diethylether and the resulting mixture stirred at room temperature for 1 h.

The reaction mixture was diluted with 100 ml of diethylether at 0° C. and treated with excess of a saturated aqueous solution of sodium sulfate. Further solid sodium sulfate was added and the organic phase was filtered to remove salts. The solvent was evaporated to dryness to give 9 g (98%) of product as an oil.

2.2. 3-(1H-Indol-3-yl)propyl bromide (Chem. Pharm. Bull. (1988), 36(8), 2853)

To a solution of 2 g (11.41 mmol) of 3-(1H-indol-3-yl) propanol in 40 ml of dioxane was added at room temperature 5.3 g (12.55 mmol) of dibromotriphenylphosphorane and the resulting solution was stirred during 18 h.

An excess of cyclohexane was added and the resulting precipitate was filtered and discarded. The solvent was evaporated to dryness to give 2.7 g (99%) of product as an oil which was used in the subsequent step without further purification.

2.3. 9-[3-(1H-Indol-3-yl)propyl]-2-pyridin-4-yl-6,7, 8,9-tetrahydro-4H-pyrimido[1,2-a]pyrimidin-4-one A suspension of 0.30 g (1.31 mmol) of 2-pyridin-4-yl-6,7, 8,9-tetrahydro-4H-pyrimido[1,2-a]pyrimidin-4-one in 8 ml of anhydrous dimethylformamide was treated with 68 mg (1.44 mmol) of sodium hydride (60% suspension in mineral oil) and the resulting mixture was heated at 70° C. for 30 min. 0.407 g (1.71 mmol) of 3-(1H-indol-3-yl)propyl bromide was added and the reaction mixture was heated at 130° C. during 18 h.

The cooled solution was treated with water and extracted with ethyl acetate. The organic phase was dried and evaporated to give crude product which was purified by silica gel chromatography, eluting with dichloromethane/methanol/ammonia in the proportions 98/2/0.2 to 90/10/1 to afford 0.3 g (59%) of pure product.
Mp: 230-232° C.

Example 3

Compound N° 15 of Table 1

9-(2-(2-Methoxyphenoxyethyl))-2-pyridin-4-yl-6,7, 8,9-tetrahydro-4H-pyrimido[1,2-a]pyrimidin-4-one (Z)-but-2-enedioate (1:1)

3.1. 9-(2-Hydroxyethyl)-2-pyridin-4-yl-6,7,8,9-tetrahydro-4H-pyrimido[1,2-a]pyrimidin-4-one A suspension of 0.30 g (1.31 mmol) of 2-pyridin-4-yl-6,7, 8,9-tetrahydro-4H-pyrimido[1,2-a]pyrimidin-4-one in 6 ml of anhydrous dimethylformamide was treated with 63 mg (1.58 mmol) of sodium hydride (60% suspension in mineral oil) and the resulting mixture was heated at 70° C. for 30 min. 0.329 g (1.58 mmol) of 2-(2-bromoethoxy)tetrahydro-2H-pyran was added and the reaction mixture was heated at 130° C. during 1 h.

The cooled solution was treated with water and extracted with ethyl acetate. The organic phase was dried and evaporated to give an oil, which was dissolved in 2 ml of methanol and treated with 0.127 g of ammonium chloride. The resulting mixture was heated for 18 h at reflux temperature.

The cooled solution was evaporated to dryness and the residue treated with water and solid potassium carbonate and extracted with dichloromethane. The organic phase was evaporated to give 0.158 g (49%) of product as an oil which was used without further purification.

3.2. 9-(2-(2-Methoxyphenoxyethyl))-2-pyridin-4-yl-6,7,8,9-tetrahydro-4H-pyrimido[1,2-a]pyrimidin-4-one (Z)-but-2-enedioate (1:1)

To a solution of 0.146 g (0.536 mmol) of 9-(2-hydroxyethyl)-2-pyridin-4-yl-6,7,8,9-tetrahydro-4H-pyrimido[1,2-a]pyrimidin-4-one in 4 ml of tetrahydrofuran under argon atmosphere, was added 0.197 g (0.75 mmol) of triphenylphosphine, 0.080 g (0.643 mmol) 2-methoxyphenol and 0.131 g (0.75 mmol) of diethylazodicarboxylate. The reaction mixture was stirred for 1 h.

The solvent was evaporated and the residue was treated with water and dilute aqueous hydrochloric acid and washed with diethylether. The aqueous phase was neutralized with solid potassium carbonate and extracted with dichloromethane. Evaporation of the organic phase gave crude product, which was purified by chromatography on silica gel, eluting with dichloromethane/methanol/ammonia in the proportions 95/5/0.5 to give 0.080 g of product in the form of a free base. Treatment with 1 equivalent of (Z)-but-2-enedioïc acid in ethanol afforded 0.060 g (23%) of product.

Mp: 140-142° C.

Example 4

Compound N° 25 of Table 1

9-[3-Phenylpropanoyl]-2-pyridin-4-yl-6,7,8,9-tetrahydro-4H-pyrimido[1,2-a]pyrimidin-4-one A suspension of 0.2 g (0.87 mmol) of 2-pyridin-4-yl-6,7,8,9-tetrahydro-4H-pyrimido[1,2-a]pyrimidin-4-one in 5 ml of chloroform was treated with 26 mg (1.14 mmol) of sodium hydride (60% suspension in mineral oil) and the resulting mixture was stirred at room temperature for 15 min and then cooled to 0° C. 0.148 g (0.964 mmol) of 3-phenylpropionyl chloride was added and the reaction mixture was stirred at room temperature during 18 h.

The reaction mixture was washed with a saturated aqueous solution of ammonium chloride and dried and evaporated. The residue was purified by chromatography on silica gel eluting with dichloromethane/methanol in the proportion 100/0 to 95/5 to afford give 0.120 mg (38%) of pure product as a white solid.

Mp: 137-140° C.

A list of chemical structures and physical data for compounds of the aforementioned formula (I) illustrating the present invention is given in table 1 and 2. The compounds have been prepared according to the methods of the example.

Example 5

Compound N° 3 of Table 2

1-[3-(1H-Indol-3-yl)propyl]-7-pyridin-4-yl-2,3-dihydroimidazo[1,2-a]pyrimidin-5(1H)-one

5.1. 7-Pyridin-4-yl-2,3-dihydroimidazo[1,2-a]pyrimidin-5(1H)-one

A mixture containing 8 g (41.4 mmol) of ethyl 3-(4-pyridyl)-3-oxopropionate and 14 g (164 mmol) of 4,5-dihydro-1H-imidazol-2-ylamine in 75 ml of ethanol was heated at reflux temperature during 18 h.

The solvent was evaporated and the crude product was purified by chromatography on silica gel eluting with a mixture of dichloromethane/methanol in the proportions 100/0 to 90/10 to obtain 6.3 g of 7-pyridin-4-yl-2,3-dihydroimidazo[1,2-a]pyrimidin-5(1H)-one as free base.

Mp: 318-320° C.

5.2. 3-(1H-Indol-3-yl)propanol (J. Med. Chem. (1995), 38(11), 1998)

To a suspension of 4.8 g (126.8 mmol) of lithium aluminum hydride in 240 ml of diethylether at 0° C. was added dropwise 10 g (52.8 mmol) of 3-(1H-indol-3-yl)propanoic acid dissolved in 430 ml of diethylether and the resulting mixture stirred at room temperature for 1 h.

The reaction mixture was diluted with 100 ml of diethylether at 0° C. and treated with excess of a saturated aqueous solution of sodium sulfate. Further solid sodium sulfate was added and the organic phase was filtered to remove salts. The solvent was evaporated to dryness to give 9 g (98%) of product as an oil.

5.3. 3-(1H-Indol-3-yl)propyl bromide (Chem. Pharm. Bull. (1988), 36(8), 2853)

To a solution of 2 g (11.41 mmol) of 3-(1H-indol-3-yl) propanol in 40 ml of dioxane was added at room temperature 5.3 g (12.55 mmol) of dibromotriphenylphosphorane and the resulting solution was stirred during 18 h.

An excess of cyclohexane was added and the resulting precipitate was filtered and discarded. The solvent was evaporated to dryness to give 2.7 g (99%) of product as an oil which was used in the subsequent step without further purification.

5.4. 1-[3-(1H-Indol-3-yl)propyl]-7-pyridin-4-yl-2,3-dihydroimidazo[1,2-a]pyrimidin-5(1H)-one To a suspension of 0.19 g (0.89 mmol) of 7-pyridin-4-yl-2,3-dihydroimidazo[1,2-a]pyrimidin-5(1H)-one in 10 ml of anhydrous N,N-dimethylformamide was added 0.135 g (0.97 mmol) of potassium carbonate and the resulting mixture was heated at 130° C. during 10 min. There is added 0.232 g (0.97 mmol) of 3-(1H-indol-3-yl)propyl bromide and heating is continued for 3 h.

The cooled suspension is treated with water, extracted with ethyl acetate and the organic extracts dried over sodium sulfate. The crude product was purified by chromatography on silica gel eluting with a mixture dichloromethane/methanol/ammonia in the ratio 90/10/1 to afford 0.18 g of pure product.

Mp: 218-220° C.

Example 6

Compound N° 16 of Table 2

1-[2-(Phenylthio)ethyl]-7-pyridin-4-yl-2,3-dihydroimidazo[1,2-a]pyrimidin-5(1H)-one hydrochloride (1:1)

To a suspension of 0.2 g (0.93 mmol) of 7-pyridin-4-yl-2,3-dihydroimidazo[1,2-a]pyrimidin-5(1H)-one in ml of anhydrous N,N-dimethylformamide was added 48.5 mg (1.21 mmol) of sodium hydride (60% suspension in mineral oil) and the resulting mixture was heated at 70° C. during 30 min. There was added 0.32 g (1.49 mmol) of 2-bromoethyl phenyl sulfide and heating was continued at 130° C. during 1 h. Water was added to the cooled mixture and the resulting solution extracted with ethyl acetate. The combined extracts were washed with water and evaporated. The crude product was purified by chromatography on silica gel eluting with a mixture of dichloromethane/methanol/diethylamine in the proportions 98/2/0.2 to obtain pure compound as free base. The compound was converted to the hydrochloride salt by addition of hydrochloric acid to an isopropylic solution of the free base. There is obtained 0.11 g of product as a yellow solid.
Mp: 199-202° C.

Example 7

Compound N° 14 of Table 2

1-[2-(4-Chlorophenoxy)ethyl]-7-pyridin-4-yl-2,3-dihydroimidazo[1,2-a]pyrimidin-5(1H-one hydrochloride (1:1)

To a suspension of 0.2 g (0.93 mmol) of 7-pyridin-4-yl-2,3-dihydroimidazo[1,2-a]pyrimidin-5(1H)-one in 5 ml of anhydrous N,N-dimethylformamide was added 48.5 mg (1.21 mmol) of sodium hydride (60% suspension in mineral oil) and the resulting mixture was heated at 70° C. for 30 min. 0.351 g (1.49 mmol) of 2-(4-chlorophenoxy)ethyl bromide was added and the reaction mixture was heated at 130° C. during 18 h.

Water was added to the cooled mixture and the resulting solution extracted with ethyl acetate. The combined extracts were washed with water and evaporated. The crude product was purified by chromatography on silica gel eluting with a mixture of dichloromethane/methanol in the proportions 100/0 to 96/4 to obtain pure compound as free base. The compound was converted to the hydrochloride salt by addition of hydrochloric acid to an ethanolic solution of the free base. There is obtained 0.24 g of product as a yellow solid.
Mp: 211-213° C.

Example 8

Compound N° 17 of Table 2

1-[-(3-Phenyl)propanoyl]-7-pyridin-4-yl-2,3-dihydroimidazo[1,2-a]pyrimidin-5(1H)-one A suspension of 0.2 g (0.93 mmol) of 7-pyridin-4-yl-2,3-dihydroimidazo[1,2-a]pyrimidin-5(1H)-one in 5 ml of N,N-dimethylformamide was treated with 48 mg (1.20 mmol) of sodium hydride (60% suspension in mineral oil) and the resulting mixture was stirred at room temperature for 15 min and then cooled to 0° C. 0.251 g (1.49 mmol) of 3-phenylpropionyl chloride was added and the reaction mixture was stirred at room temperature during 18 h.

The reaction mixture was washed with a saturated aqueous solution of ammonium chloride and dried and evaporated. The residue was purified by chromatography on silica gel eluting with dichloromethane/methanol in the proportion 100/0 to 95/5 to afford give 0.2 g of pure product as a white solid.
Mp: 171-172° C.

In the table, R1 is an unsubstituted 4-pyridyl group, Ph represents a phenyl group, in the column "X", when X represents two hydrogen atoms, only "H" is indicated, and in the column R2, "_____" indicates the bond attached to the Y group.

TABLE 1

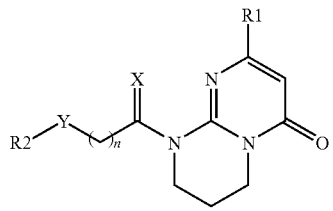

(I)

| N° | X | Y | R2 | n | Mp ° C. | salt |
|---|---|---|---|---|---|---|
| 1 | H | CH₂ | (3-indolyl) | 0 | 217-219 | (1:1) (+/−) 2,3-dihydroxybutanedioate |
| 2 | H | CH₂ | Ph | 1 | 130-132 | (1:1) (Z)-but-2-enedioate |
| 3 | H | CH₂ | Ph | 0 | 141-143 | (1:1) (Z)-but-2-enedioate |
| 4 | H | CH₂ | (3-indolyl) | 1 | 230-232 | base |
| 5 | H | O | Ph | 1 | 190-192 | (1:1) (Z)-but-2-enedioate |
| 6 | H | CH₂ | (benzo[1,3]dioxol-5-yl) | 1 | 150-152 | (1:1) (Z)-but-2-enedioate |

TABLE 1-continued

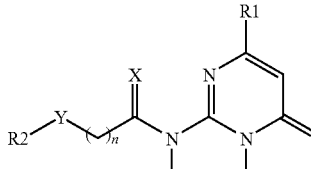
(I)

| # | R1 | Y | R2 | n | mp (°C) | salt |
|---|----|----|----|----|---------|------|
| 7 | H | CH₂ | 2-methoxyphenyl (H₃C-O-C₆H₄-) | 0 | 157-160 | (1:1) (Z)-but-2-enedioate |
| 8 | H | O | 4-fluorophenyl | 1 | 161-163 | (1:1) (Z)-but-2-enedioate |
| 9 | H | CH₂ | 2-chlorophenyl | 1 | 128-130 | (1:1) (Z)-but-2-enedioate |
| 10 | H | CH₂ | 4-methylphenyl | 1 | 157-159 | (1:1) (Z)-but-2-enedioate |
| 11 | H | CH₂ | 4-trifluoromethylphenyl | 1 | 160-162 | (1:1) (Z)-but-2-enedioate |
| 12 | H | CH₂ | Ph | 2 | 156-158 | (1:1) (Z)-but-2-enedioate |
| 13 | H | CH₂ | 2-methylphenyl | 1 | 160-162 | (1:1) (Z)-but-2-enedioate |
| 14 | H | CH₂ | 2,4-dimethoxy-3-methylphenyl | 0 | 160-162 | (1:1) (Z)-but-2-enedioate |
| 15 | H | O | 2-methoxyphenyl | 1 | 140-142 | (1:1) (Z)-but-2-enedioate |
| 16 | H | CH₂ | 2-methoxyphenyl | 1 | 153-155 | (1:1) (Z)-but-2-enedioate |

TABLE 1-continued
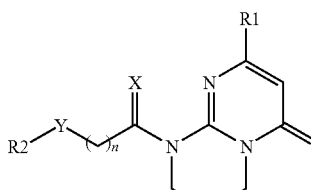
(I)
| | R2 | Y | (aryl) | n | mp (°C) | salt |
|---|---|---|---|---|---|---|
| 17 | H | O | 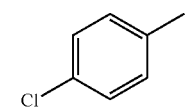 4-Cl-C6H4 | 1 | 223-225 | (1:1) hydrochloride |
| 18 | H | CH2 | 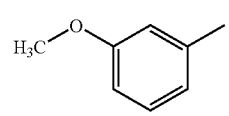 3-MeO-C6H4 | 1 | 238-240 | (1:1) hydrochloride |
| 19 | H | bond | 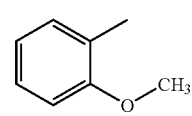 2-MeO-C6H4 | 0 | 258-260 | (1:1) hydrochloride |
| 20 | H | S | Ph | 1 | 215-217 | (1:1) hydrochloride |
| 21 | H | CH2 | 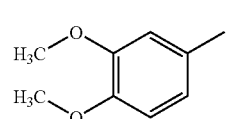 3,4-(MeO)2-C6H3 | 1 | 176-178 | (1:1) hydrochloride |
| 22 | H | CH2 | 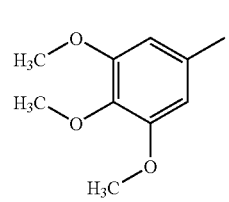 3,4,5-(MeO)3-C6H2 | 1 | 225-227 | (1:1) hydrochloride |
| 23 | H | SO2 | Ph | 1 | 254-256 | (1:1) hydrochloride |
| 24 | H | CH2 | 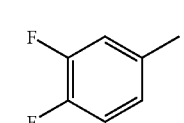 3,4-F2-C6H3 | 1 | 215-217 | (1:1) hydrochloride |
| 25 | O | CH2 | Ph | 1 | 137-140 | base |
| 26 | H | CH2 | 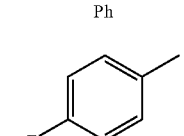 4-F-C6H4 | 1 | 245-247 | (1:1) hydrochloride |
| 27 | H | CH2 | 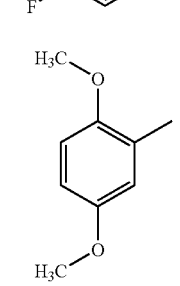 2,5-(MeO)2-C6H3 | 1 | 245-247 | (1:1) hydrochloride |

TABLE 1-continued
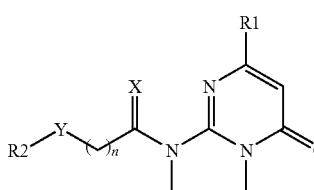
(I)
| # | R2 | Y | R group | n | mp (°C) | form |
|---|---|---|---|---|---|---|
| 28 | H | CH$_2$ | 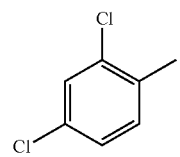 | 1 | 208-210 | (1:1) hydrochloride |
| 29 | H | CH$_2$ | 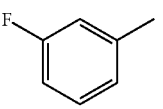 | 1 | 221-223 | (1:1) hydrochloride |
| 30 | H | CH$_2$ | 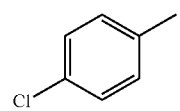 | 1 | 222-224 | (1:1) hydrochloride |
| 31 | H | CH$_2$ | 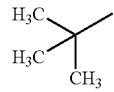 | 0 | 166-167 | base |
| 32 | H | CH$_2$ | 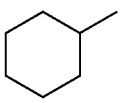 | 0 | 134-135 | base |
| 33 | H | CH$_2$ | 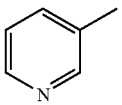 | 1 | 81.5 | base |
| 34 | H | CH$_2$ | 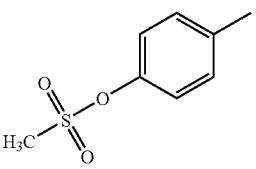 | 0 | 148.8 | base |
| 35 | H | CH$_2$ |  | 0 | 137.4 | base |
| 36 | H | PhCH | Ph | 1 | 154.3 | base |
| 37 | H | CH$_2$ |  | 2 | 89.3 | base |
| 38 | H | CH$_2$ | 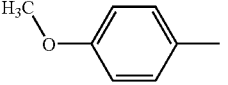 | 2 | 140.4 | base |

TABLE 1-continued
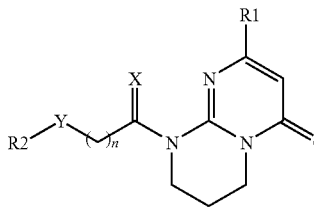
(I)
| N° | X | Y | R2 | n | m.p. (°C) | salt |
|---|---|---|---|---|---|---|
| 39 | H | CH$_2$ | 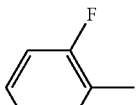 | 1 | 243-245 | (1:1) hydrochloride |
| 40 | H | ≡ | Ph | 0 | 235-237 | (1:1) hydrochloride |
| 41 | H | CHCH$_3$ | Ph | 1 | 222-224 | (1:1) hydrochloride |
| 42 | H | CH$_2$ | 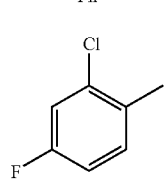 | 0 | 268-272 | (1:1) hydrochloride |
| 43 | H | CO | Ph | 0 | 284-286 | (1:1) hydrochoride |
| N° | X | Y | R2 | n | [M + H]$^+$ Observed | salt |
|---|---|---|---|---|---|---|
| 44 | H | O | 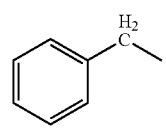 | 2 | 391 | base |
| 45 | H | CH$_2$ | SMe | 2 | 331 | base |
| 46 | H | CH$_2$ | 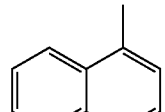 | 0 | 383 | base |
| 47 | H | CH$_2$ | 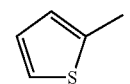 | 0 | 339 | base |
| 48 | H | CH$_2$ | 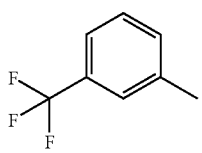 | 0 | 401 | base |
| 49 | H | CH$_2$ | 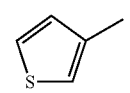 | 0 | 339 | base |
| 50 | H | CH$_2$ | 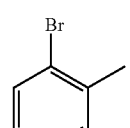 | 0 | 412 | base |

TABLE 1-continued
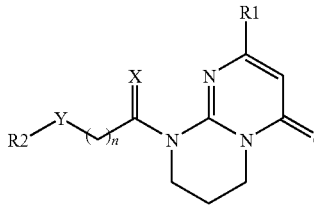
(I)
| | | | | | | |
|---|---|---|---|---|---|---|
| 51 | H | CH₂ | 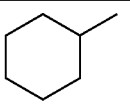 | 2 | 367 | base |
| 52 | H | CH₂ | 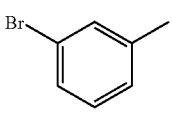 | 0 | 412 | base |
| 53 | H | CH₂ | 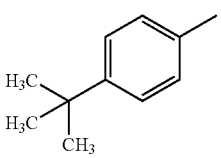 | 0 | 389 | base |
| 54 | H | CH₂ | 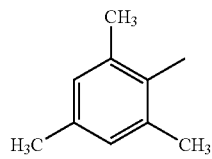 | 0 | 375 | base |
| 55 | H | CH₂ | 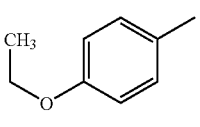 | 0 | 377 | base |
| 56 | H | CH₂ | 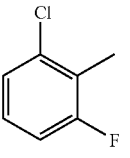 | 0 | 385 | base |
| 57 | H | CH₂ | 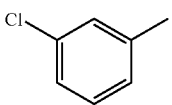 | 0 | 367 | base |
| 58 | H | CH₂ | 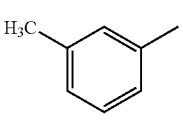 | 0 | 347 | base |
| 59 | H | CHCH₃ | OCH₃ | 1 | 315 | base |
| 60 | H | CH₂ | 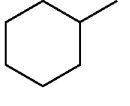 | 1 | 353 | base |
| 61 | H | 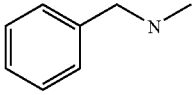 | 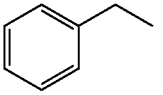 | 2 | 466 | Base |

TABLE 1-continued

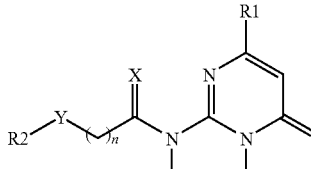
(I)

| | R2 | Y | R1 | n | mp | salt |
|---|---|---|---|---|---|---|
| 62 | H | 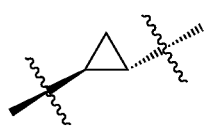 racemate | Ph | 0 | 213-216 | Hydrochloride |
| 63 | H | 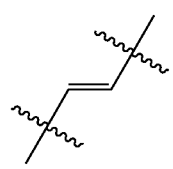 | Ph | 0 | 264-266 | Hydrochloride |
| 64 | H | C(OH)(CH$_3$) racemate | Ph | 0 | 126-129 | (Z)-but-enedioate |
| 65 | H | CO | 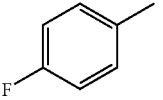 | 1 | 226-229 | hydrochloride |
| 66 | H | CH$_2$ |  | 1 | 254-256 | hydrochloride |
| 67 | H | CO | Ph | 1 | 136-138 | (Z)-but-enedioate |
| 68 | H | CH(OH) | Ph | 1 | 147-149 | base |
| 69 | H | CH(OH) racemate |  | 0 | 248-250 | hydrochloride |
| 70 | H | CH(OH) (+)-(R) | Ph | 0 | 232-234 | hydrochloride |
| 71 | H | CH(OH) (−)-(S) | Ph | 0 | 220-222 | hydrochloride |
| 72 | H | CH(OH) racemate | 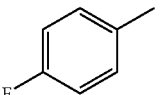 | 1 | 145-147 | base |
| 73* | H, CH$_3$ (rac) | CO | Ph | 0 | 194-196 | hydrochloride |
| 74* | H, CH$_3$ (rac) | CH(OH) racemate | Ph | 0 | 232-234 | base |
| 75 | H | CO | 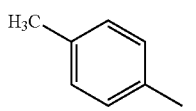 | 0 | 263-264 | hydrochloride |
| 76 | H | CO | 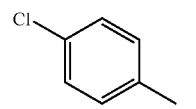 | 0 | 247 | hydrochloride |

TABLE 1-continued (I)

| | | | | | | |
|---|---|---|---|---|---|---|
| 77 | H | CO | 4-fluorophenyl | 0 | 245 | hydrochloride |
| 78 | H | CO | biphenyl-4-yl | 0 | 140-141 | hydrochloride |
| 79 | H | CO | 3-methoxyphenyl | 0 | 204-205 | hydrochloride |
| 80 | H | CO | naphthalen-2-yl | 0 | 217-218 | hydrochloride |
| 81 | H | CO | 5,5,8,8-tetramethyl-5,6,7,8-tetrahydronaphthalen-2-yl | 0 | 209-210 | Hydrochloride |
| 82* | H, CH$_3$ (rac) | CO | 4-methoxy-6-methyl-benzo[1,3]dioxol-? | 0 | 233-234 | hydrochloride |
| 83 | H | CH(OH) racemate | 2,5-dimethylphenyl | 0 | 157-158 | base |
| 84 | H | CH(OH) racemate | 5,5,8,8-tetramethyl-5,6,7,8-tetrahydronaphthalen-2-yl | 0 | 248-249 | Base |
| 85 | H | CO | phenylamino | 0 | 220-222 | Base |

TABLE 1-continued
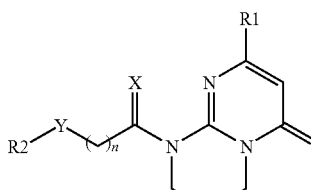
(I)
| N° | R1 | X | R2 | n | Mp ° C. | salt |
|---|---|---|---|---|---|---|
| 86 | H | CO | 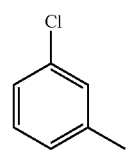 | 0 | 263-265 | hydrochloride |
| 87 | H | CH(OH) racemate | 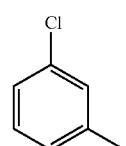 | 0 | 172-174 | base |
| 88 | H | CO | 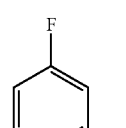 | 0 | 273-275 | hydrochloride |
| 89 | H | CH(OH) racemate | 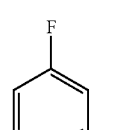 | 0 | 96-98 | base |
TABLE 2
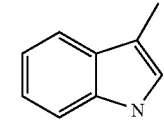
| N° | R1 | Y | X | R2 | n | Mp ° C. | salt |
|---|---|---|---|---|---|---|---|
| 1 | 4-py | CH$_2$ | H | 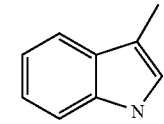 | 0 | 205-207 | (Z)-but-enedioate |
| 2 | 4-py | CH$_2$ | H | Ph | 1 | 258-260 | (Z)-but-enedioate |
| 3 | 4-py | CH$_2$ | H | 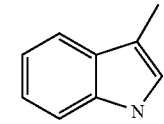 | 1 | 218-220 | base |
| 4 | 4-py | CH$_2$ | H | Ph | 0 | 158-160 | (Z)-but-enedioate |

TABLE 2-continued
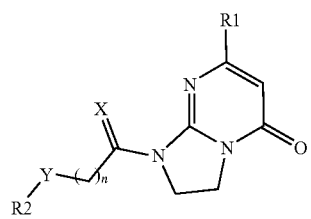
| N° | R1 | Y | X | R2 | n | Mp °C. | salt |
|----|-----|-----|---|-----|---|--------|------|
| 5 | 4-py | CH$_2$ | H | 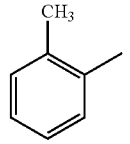 | 1 | 224-225 | hydrochloride |
| 6 | 4-py | CH$_2$ | H | 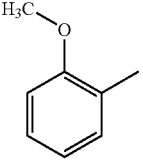 | 1 | 228-229 | hydrochloride |
| 7 | 4-py | CH$_2$ | H | Ph | 2 | 238.5-240 | hydrochloride |
| 8 | 4-py | CH$_2$ | H | 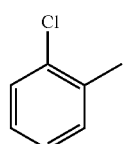 | 1 | 222-223 | hydrochloride |
| 9 | 4-py | CH$_2$ | H | 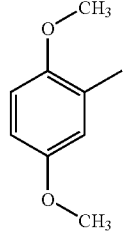 | 1 | 208-209 | hydrochloride |
| 10 | 4-py | CH$_2$ | H | 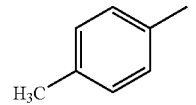 | 1 | 227-228 | hydrochloride |
| 11 | 4-py | CH$_2$ | H | 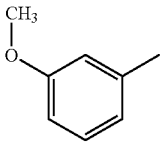 | 1 | 190-191 | hydrochloride |
| 12 | 4-py | CH$_2$ | H | 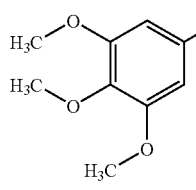 | 1 | 197-201 | hydrochloride |

TABLE 2-continued
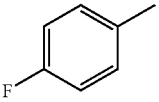
| N° | R1 | Y | X | R2 | n | Mp ° C. | salt |
|---|---|---|---|---|---|---|---|
| 13 | 4-py | O | H | 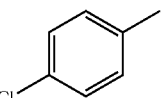 | 1 | 205-207 | hydrochloride |
| 14 | 4-py | O | H | 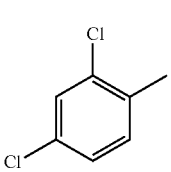 | 1 | 211-213 | Hydrochloride |
| 15 | 4-py | CH$_2$ | H | 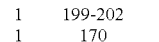 | 1 | 207-208 | hydrochloride |
| 16 | 4-py | S | H | Ph | 1 | 199-202 | hydrochloride |
| 17 | 4-py | CH$_2$ | O | Ph | 1 | 170 | base |
| 18 | 4-py | CH$_2$ | H | 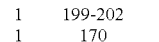 | 1 | 251-252 | hydrochloride |
| 19 | 4-py | CH$_2$ | H | 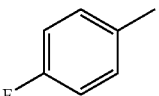 | 1 | 187-188 | hydrochloride |
| 20 | 4-py | CH$_2$ | H | 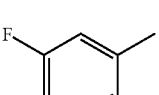 | 0 | 117-118 | base |
| 21 | 4-py | CH$_2$ | H | 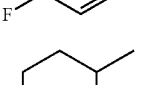 | 0 | 142-143 | base |
| 22 | 4-py | CO | H | Ph | 0 | 252-256 | hydrochloride |
| 23 | 4-py | CH(OH) (S) | H | CF$_3$ | 1 | 191-192 | base |
| 24 | 4-py | = (trans) | H | CF$_3$ | 0 | 136-138 | base |
| 25 | 4-py | CH$_2$ | H | 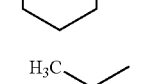 | 1 | 136-137 | base |
| 26 | 4-py | CH(OH) (R) | H | CF3 | 1 | 187-189 | base |
| 27 | 4-py | CH$_2$ | H |  | 1 | 201-203 | hydrochloride |

TABLE 2-continued
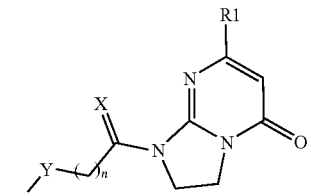
| N° | R1 | Y | X | R2 | n | Mp ° C. | salt |
|---|---|---|---|---|---|---|---|
| 28 | 4-py | CH₂ | H | 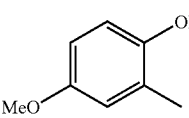 | 0 | 221-223 | hydrochloride |
| 29 | 4-py | SO₂ | H | Ph | 1 | 261-264 | base |
| 30 | 4-py | CH₂ | H | CF₃ | 1 | 261-263 | hydrochloride |
| 31 | 4-py | CH₂ | H | 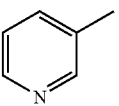 | 1 | 186-187 | hydrochloride |
| 32 | 4-py | CH₂ | H | 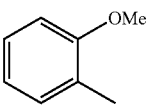 | 0 | 240-242 | hydrochloride |
| 33 | 4-py | CO | H | 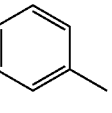 | 0 | 241-242 | hydrochloride |
| 34 | 4-py | CO | H | 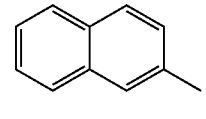 | 0 | 284-285 | hydrochloride |
| 35 | 4-py | CO | CH₃ (Rac) | 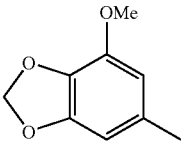 | 0 | 252-253 | hydrochloride |
| 36 | 4-py | CO | H | 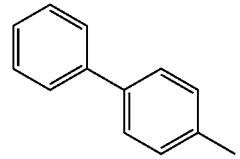 | 0 | 238-239 | hydrochloride |
| 37 | 4-py | CO | H | 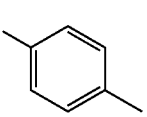 | 0 | 226-227 | hydrochloride |
| 38 | 4-py | CO | H | 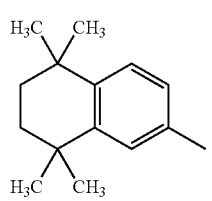 | 0 | 233-234 | Hydrochloride |

TABLE 2-continued

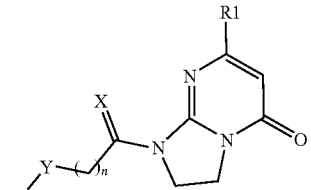

| N° | R1 | Y | X | R2 | n | Mp ° C. | salt |
|---|---|---|---|---|---|---|---|
| 39 | 4-py | CO | H | 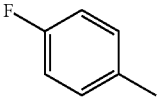 | 0 | 250-251 | Hydrochloride |
| 40 | 4-py | CO | H | 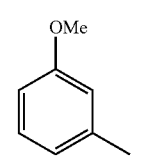 | 0 | 238-239 | hydrochloride |

Test Example

Inhibitory Activity of the Medicament of the Present Invention Against GSK3β

Two different protocols can be used.

In a first protocol: 7.5 μM of prephosphorylated GS1 peptide and 10 μM ATP (containing 300,000 cpm of 33P-ATP) were incubated in 25 mM Tris-HCl, pH 7.5, 0.6 mM DTT, 6 mM MgCl$_2$, 0.6 mM EGTA, 0.05 mg/ml BSA buffer for 1 hour at room temperature in the presence of GSK3beta (total reaction volume: 100 microliters).

In a second protocol: 4.1 μM of prephosphorylated GS1 peptide and 42 μM ATP (containing 260,000 cpm 33P-ATP) were incubated in 80 mM Mes-NaOH, pH 6.5, 1 mM Mg acetate, 0.5 mM EGTA, 5 mM 2-mercaptoethanol, 0.02% Tween 20, 10% glycerol buffer for 2 hours at room temperature in the presence of GSK3beta. Inhibitors were solubilized in DMSO (final solvent concentration in the reaction medium, 1%).

The reaction was stopped with 100 microliters of a solution made of 25 g polyphosphoric acid (85% P$_2$O$_5$), 126 ml 85% H$_3$PO$_4$, H$_2$O to 500 ml and then diluted to 1:100 before use. An aliquot of the reaction mixture was then transferred to Whatman P81 cation exchange filters and rinsed with the solution described above. Incorporated 33P radioactivity was determined by liquid scintillation spectrometry. The phosphorylated GS-1 peptide had the following sequence: NH2-YRRAAVPPSPSLSRHSSPHQS(P)EDEE-COOH.

The GSK3β inhibitory activity of the compounds of the present invention are expressed in IC$_{50}$, and as an illustration the range of IC$_{50}$'s of the compounds in table 1 is between 2 nanomolar to 1 micromolar concentrations.

Formulation Example (1) Tablets

The ingredients below were mixed by an ordinary method and compressed by using a conventional apparatus.

| | |
|---|---|
| Compound of Example 1 | 30 mg |
| Crystalline cellulose | 60 mg |
| Corn starch | 100 mg |
| Lactose | 200 mg |
| Magnesium stearate | 4 mg |

(2) Soft Capsules

The ingredients below were mixed by an ordinary method and filled in soft capsules.

| | |
|---|---|
| Compound of Example 1 | 30 mg |
| Olive oil | 300 mg |
| Lecithin | 20 mg |

(1) Parenteral Preparations

The ingredients below were mixed by an ordinary method to prepare injections contained in a 1 ml ampoule.

| | |
|---|---|
| Compound of Example 1 | 3 mg |
| Sodium chloride | 4 mg |
| Distilled water for injection | 1 ml |

INDUSTRIAL APPLICABILITY

The compounds of the present invention have GSK3β inhibitory activity and are useful as an active ingredient of a medicament for preventive and/or therapeutic treatment of neurodegenerative diseases caused by abnormal activity of GSK3β.

What is claimed is:

1. A method of inhibiting the activity of glycogen synthase kinase 3-beta (GSK3-β), which comprises administering to a patient in need of said inhibition a therapeutically effective amount of a compound of formula (I) or a pharmaceutically acceptable salt thereof:

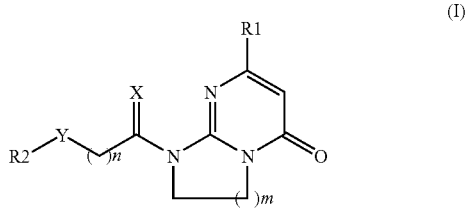

wherein:
X represents two hydrogen atoms, a sulfur atom, an oxygen atom or a $C_{1-2}$ alkyl group and a hydrogen atom;
Y represents a bond, an ethenylene group, an ethynylene group, a 1,2-cyclopropylene, an oxygen atom, a sulfur atom, a sulfonyl group, a sulfinyl group, a carbonyl group, an NH group being optionally substituted by a $C_{1-6}$ alkyl group, a phenyl or a benzyl group; or a methylene group optionally substituted by one or two groups chosen from a $C_{1-6}$ alkyl group, a phenyl group, a hydroxyl group and a $C_{1-4}$ alkoxy group;
R1 represents a 2, 3 or 4-pyridyl group optionally substituted by a $C_{3-6}$ cycloalkyl group, a $C_{1-4}$ alkyl group, a $C_{1-4}$ alkoxy group, a benzyl group or a halogen atom;
when Y represents a bond, a 1,2-cyclopropylene, a methylene group optionally substituted or a carbonyl group then R2 represents a $C_{1-6}$ alkyl group, a $C_{3-6}$ cycloalkyl group, a $C_{1-4}$ alkylthio group, a $C_{1-4}$ alkoxy group, a perhalogenated alkyl group, a $C_{1-3}$ halogenated alkyl group, a 5,6,7,8-tetrahydronaphthyl ring, a naphthyl ring, a phenylthio group, a benzyl group, a phenyl ring, a pyridyl ring, an indole ring, a pyrrole ring, a thiophene ring, a furan ring or an imidazole ring; the benzyl group or the rings being optionally substituted by 1 to 4 substituents selected from a $C_{1-6}$ alkyl group, a methylenedioxy group, a halogen atom, a $C_{1-2}$ perhalogenated alkyl group, a $C_{1-3}$ halogenated alkyl group, a hydroxyl group, a $C_{1-4}$ alkoxy group, a nitro, a cyano, an amino, a $C_{1-5}$ monoalkylamino group, a $C_{2-10}$ dialkyl-amino group, a $C_{1-6}$ alkylcarbonylamino group, a $C_{6,10}$ arylcarbonylamino group, a $C_{1-4}$ alkyl-sulfonyl group, $C_{1-4}$ alkylsulfonyloxy group and a phenyl group;
when Y represents an ethenylene group, an ethynylene group, an oxygen atom, a sulfur atom, a sulfonyl group, a sulfinyl group or an NH group being optionally substituted then R2 represents a $C_{1-6}$ alkyl group, a $C_{3-6}$ cycloalkyl group, a $C_{1-2}$ perhalogenated alkyl group, a $C_{1-3}$ halogenated alkyl group, a naphthyl ring, a 5,6,7,8-tetrahydronaphthyl ring, a benzyl group, a phenyl ring, a pyridyl ring, an indole ring, a pyrrole ring, a thiophene ring, a furan ring or an imidazole ring; the benzyl group or the rings being optionally substituted by 1 to 4 substituents selected from a $C_{1-6}$ alkyl group, a methylenedioxy group, a halogen atom, a $C_{1-2}$ perhalogenated alkyl group, a $C_{1-3}$ halogenated alkyl group, a hydroxyl group, a $C_{1-4}$ alkoxy group, a nitro, a cyano, an amino, a $C_{1-5}$ monoalkylamino group, a $C_{2-10}$ dialkylamino group, a $C_{1-6}$ alkylcarbonylamino group, a $C_{6,10}$ arylcarbonylamino group, a $C_{1-4}$ alkylsulfonyl group, a $C_{1-4}$ alkylsulfonyloxy group and a phenyl group;
m represents 1 or 2;
and n represents 0 to 3.

2. The method according to claim 1, wherein in said compound of formula I, R1 represents an unsubstituted 4-pyridyl group.

3. The method according to claim 2, wherein in said compound according to formula I, R2 represents a $C_{1-4}$ alkyl group, $C_{1-2}$ alkylthio group, $C_{1-2}$ alkoxy group, a trifluoromethyl group, a $C_{5-6}$ cycloalkyl group, a naphthyl ring, a 5,6,7,8-tetrahydronaphthyl ring, a phenyl ring, a pyridyl ring, an indole ring, a thiophene ring; the rings being optionally substituted by 1 to 4 substituents.

4. The method according to claim 1, wherein said compound of formula I is selected from the group consisting of:
9-[2-(1H-indol-3-yl)ethyl]-2-pyridin-4-yl-6,7,8,9-tetrahydro-4H-pyrimido[1,2-a]pyrimidin-4-one;
9-(3-phenylpropyl)-2-pyridin-4-yl-6,7,8,9-tetrahydro-4H-pyrimido[1,2-a]pyrimidin-4-one;
9-(2-phenylethyl)-2-pyridin-4-yl-6,7,8,9-tetrahydro-4H-pyrimido[1,2-a]pyrimidin-4-one;
9-[3-(1H-indol-3-yl)propyl]-2-pyridin-4-yl-6,7,8,9-tetrahydro-4H-pyrimido[1,2-a]pyrimidin-4-one;
9-(2-phenoxyethyl)-2-pyridin-4-yl-6,7,8,9-tetrahydro-4H-pyrimido[1,2-a]pyrimidin-4-one;
9-[3-(3,4-methylenedioxyphenyl)propyl]-2-pyridin-4-yl-6,7,8,9-tetrahydro-4H-pyrimido[1,2-a]pyrimidin-4-one;
9-[2-(2-methoxyphenyl)ethyl]-2-pyridin-4-yl-6,7,8,9-tetrahydro-4H-pyrimido[1,2-a]pyrimidin-4-one;
9-[2-(4-fluorophenoxyethyl)]-2-pyridin-4-yl-6,7,8,9-tetrahydro-4H-pyrimido[1,2-a]pyrimidin-4-one;
9-[3-(2-chlorophenyl)propyl]-2-pyridin-4-yl-6,7,8,9-tetrahydro-4H-pyrimido[1,2-a]pyrimidin-4-one;
9-[3-(4-methylphenyl)propyl]-2-pyridin-4-yl-6,7,8,9-tetrahydro-4H-pyrimido[1,2-a]pyrimidin-4-one;
9-[3-(4-trifluoromethylphenyl)propyl]-2-pyridin-4-yl-6,7,8,9-tetrahydro-4H-pyrimido[1,2-a]pyrimidin-4-one;
9-(4-phenylbutyl)-2-pyridin-4-yl-6,7,8,9-tetrahydro-4H-pyrimido[1,2-a]pyrimidin-4-one;
9-[3-(2-methylphenyl)propyl]-2-pyridin-4-yl-6,7,8,9-tetrahydro-4H-pyrimido[1,2-a]pyrimidin-4-one;
9-[2-(2,5-dimethoxyphenyl)ethyl]-2-pyridin-4-yl-6,7,8,9-tetrahydro-4H-pyrimido[1,2-a]pyrimidin-4-one;
9-[2-(2-methoxyphenoxy)ethyl]-2-pyridin-4-yl-6,7,8,9-tetrahydro-4H-pyrimido[1,2-a]pyrimidin-4-one;
9-[3-(2-methoxyphenyl)propyl]-2-pyridin-4-yl-6,7,8,9-tetrahydro-4H-pyrimido[1,2-a]pyrimidin-4-one;
9-[2-(4-chlorophenoxy)ethyl]-2-pyridin-4-yl-6,7,8,9-tetrahydro-4H-pyrimido[1,2-a]pyrimidin-4-one;
9-[3-(3-methoxyphenyl)propyl]-2-pyridin-4-yl-6,7,8,9-tetrahydro-4H-pyrimido[1,2-a]pyrimidin-4-one;
9-(2-methoxyphenylmethyl)-2-pyridin-4-yl-6,7,8,9-tetrahydro-4H-pyrimido[1,2-a]pyrimidin-4-one;
9-[2-phenylthioethyl]-2-pyridin-4-yl-6,7,8,9-tetrahydro-4H-pyrimido[1,2-a]pyrimidin-4-one;
9-[3-(3,4-dimethoxyphenyl)propyl]-2-pyridin-4-yl-6,7,8,9-tetrahydro-4H-pyrimido[1,2-a]pyrimidin-4-one;
9-[3-(3,4,5-trimethoxyphenyl)propyl]-2-pyridin-4-yl-6,7,8,9-tetrahydro-4H-pyrimido[1,2-a]pyrimidin-4-one;
9-[2-(phenylsulfonyl)ethyl]-2-pyridin-4-yl-6,7,8,9-tetrahydro-4H-pyrimido[1,2-a]pyrimidin-4-one;
9-[3-(3,4-fluorophenyl)propyl]-2-pyridin-4-yl-6,7,8,9-tetrahydro-4H-pyrimido[1,2-a]pyrimidin-4-one;
9-[3-phenylpropanoyl]-2-pyridin-4-yl-6,7,8,9-tetrahydro-4H-pyrimido[1,2-a]pyrimidin-4-one;
9-[3-(4-fluorophenyl)propyl]-2-pyridin-4-yl-6,7,8,9-tetrahydro-4H-pyrimido[1,2-a]pyrimidin-4-one;
9-[3-(2,5-dimethoxyphenyl)propyl]-2-pyridin-4-yl-6,7,8,9-tetrahydro-4H-pyrimido[1,2-a]pyrimidin-4-one;

9-[3-(2,4-dichlorophenyl)propyl]-2-pyridin-4-yl-6,7,8,9-tetrahydro-4H-pyrimido[1,2-a]pyrimidin-4-one;
9-[3-(3-fluorophenyl)propyl]-2-pyridin-4-yl-6,7,8,9-tetrahydro-4H-pyrimido[1,2-a]pyrimidin-4-one;
9-[3-(4-chlorophenyl)propyl]-2-pyridin-4-yl-6,7,8,9-tetrahydro-4H-pyrimido[1,2-a]pyrimidin-4-one;
9-(3,3-dimethylbutyl)-2-pyridin-4-yl-6,7,8,9-tetrahydro-4H-pyrimido[1,2-a]pyrimidin-4-one;
9-(2-cyclohexylethyl)-2-pyridin-4-yl-6,7,8,9-tetrahydro-4H-pyrimido[1,2-a]pyrimidin-4-one;
9-[3-(pyridin-3-yl)propyl]-2-pyridin-4-yl-6,7,8,9-tetrahydro-4H-pyrimido[1,2-a]pyrimidin-4-one;
9-[2-(4-methylsulfonyloxyphenyl)ethyl]-2-pyridin-4-yl-6,7,8,9-tetrahydro-4H-pyrimido[1,2-a]pyrimidin-4-one;
9-(3-methylbutyl)-2-pyridin-4-yl-6,7,8,9-tetrahydro-4H-pyrimido[1,2-a]pyrimidin-4-one;
9-(3,3-diphenylpropyl)-2-pyridin-4-yl-6,7,8,9-tetrahydro-4H-pyrimido[1,2-a]pyrimidin-4-one;
9-[4-(4-methoxyphenyl)butyl]-2-pyridin-4-yl-6,7,8,9-tetrahydro-4H-pyrimido[1,2-a]pyrimidin-4-one;
9-[4-(4-nitrophenyl)butyl]-2-pyridin-4-yl-6,7,8,9-tetrahydro-4H-pyrimido[1,2-a]pyrimidin-4-one;
9-[3-(2-fluorophenyl)propyl]-2-pyridin-4-yl-6,7,8,9-tetrahydro-4H-pyrimido[1,2-a]pyrimidin-4-one;
9-(3-phenylprop-2-ynyl)-2-pyridin-4-yl-6,7,8,9-tetrahydro-4H-pyrimido[1,2-a]pyrimidin-4-one;
9-(3-phenylbutyl)-2-pyridin-4-yl-6,7,8,9-tetrahydro-4H-pyrimido[1,2-a]pyrimidin-4-one;
9-[2-(2-chloro-4-fluorophenyl)ethyl]-2-pyridin-4-yl-6,7,8,9-tetrahydro-4H-pyrimido[1,2-a]pyrimidin-4-one;
9-(2-phenyl-2-oxo-ethyl)-2-pyridin-4-yl-6,7,8,9-tetrahydro-4H-pyrimido[1,2-a]pyrimidin-4-one;
9-(3-benzyloxypropyl)-2-pyridin-4-yl-6,7,8,9-tetrahydro-4H-pyrimido[1,2-a]pyrimidin-4-one;
9-(3-methylthiobutyl)-2-pyridin-4-yl-6,7,8,9-tetrahydro-4H-pyrimido[1,2-a]pyrimidin-4-one;
9-[2-(1-naphthyl)ethyl]-2-pyridin-4-yl-6,7,8,9-tetrahydro-4H-pyrimido[1,2-a]pyrimidin-4-one;
9-[2-(thiophen-2-yl)ethyl]-2-pyridin-4-yl-6,7,8,9-tetrahydro-4H-pyrimido[1,2-a]pyrimidin-4-one;
9-[2-(3-trifluoromethylphenyl)ethyl]-2-pyridin-4-yl-6,7,8,9-tetrahydro-4H-pyrimido[1,2-a]pyrimidin-4-one;
9-[(2-(thiophen-3-yl)ethyl]-2-pyridin-4-yl-6,7,8,9-tetrahydro-4H-pyrimido[1,2-a]pyrimidin-4-one;
9-[2-(2-bromophenyl)ethyl]-2-pyridin-4-yl-6,7,8,9-tetrahydro-4H-pyrimido[1,2-a]pyrimidin-4-one;
9-(4-cyclohexylbutyl)-2-pyridin-4-yl-6,7,8,9-tetrahydro-4H-pyrimido[1,2-a]pyrimidin-4-one;
9-[2-(3-bromophenyl)ethyl]-2-pyridin-4-yl-6,7,8,9-tetrahydro-4H-pyrimido[1,2-a]pyrimidin-4-one;
9-[2-(4-ter-butylphenyl)ethyl]-2-pyridin-4-yl-6,7,8,9-tetrahydro-4H-pyrimido[1,2-a]pyrimidin-4-one;
9-[2-(2,4,6-trimethylphenyl)ethyl]-2-pyridin-4-yl-6,7,8,9-tetrahydro-4H-pyrimido[1,2-a]pyrimidin-4-one;
9-[2-(4-ethoxyphenyl)ethyl]-2-pyridin-4-yl-6,7,8,9-tetrahydro-4H-pyrimido[1,2-a]pyrimidin-4-one;
9-[2-(2-chloro-6-fluorophenyl)ethyl]-2-pyridin-4-yl-6,7,8,9-tetrahydro-4H-pyrimido[1,2-a]pyrimidin-4-one;
9-[2-(3-chlorophenyl)ethyl]-2-pyridin-4-yl-6,7,8,9-tetrahydro-4H-pyrimido[1,2-a]pyrimidin-4-one;
9-[2-(3-methylphenyl)ethyl]-2-pyridin-4-yl-6,7,8,9-tetrahydro-4H-pyrimido[1,2-a]pyrimidin-4-one;
9-(3-methoxybutyl)-2-pyridin-4-yl-6,7,8,9-tetrahydro-4H-pyrimido[1,2-a]pyrimidin-4-one;
9-(3-cyclohexylpropyl)-2-pyridin-4-yl-6,7,8,9-tetrahydro-4H-pyrimido[1,2-a]pyrimidin-4-one;
9-[3-[di(phenylmethyl)amino]propyl]-2-pyridin-4-yl-6,7,8,9-tetrahydro-4H-pyrimido[1,2-a]pyrimidin-4-one;
9-(2-phenyl-cyclopropylmethyl)-2-pyridin-4-yl-6,7,8,9-tetrahydro-4H-pyrimido[1,2-a]pyrimidin-4-one;
9-(3-phenylprop-2-enyl)-2-pyridin-4-yl-6,7,8,9-tetrahydro-4H-pyrimido[1,2-a]pyrimidin-4-one;
9-(2-phenyl-2-hydroxypropyl)-2-pyridin-4-yl-6,7,8,9-tetrahydro-4H-pyrimido[1,2-a]pyrimidin-4-one;
9-[3-(4-fluorophenyl)-3-oxo-propyl]-2-pyridin-4-yl-6,7,8,9-tetrahydro-4H-pyrimido[1,2-a]pyrimidin-4-one;
9-(4,4,4-trifluorobutyl)-2-pyridin-4-yl-6,7,8,9-tetrahydro-4H-pyrimido[1,2-a]pyrimidin-4-one;
9-[3-phenyl-3-oxo-propyl]-2-pyridin-4-yl-6,7,8,9-tetrahydro-4H-pyrimido[1,2-a]pyrimidin-4-one;
9-[3-phenyl-3-hydroxypropyl]-2-pyridin-4-yl-6,7,8,9-tetrahydro-4H-pyrimido[1,2-a]pyrimidin-4-one;
9-[3,3,3-trifluoro-2-hydroxypropyl]-2-pyridin-4-yl-6,7,8,9-tetrahydro-4H-pyrimido[1,2-a]pyrimidin-4-one;
(R)-9-[2-phenyl-2-hydroxyethyl]-2-pyridin-4-yl-6,7,8,9-tetrahydro-4H-pyrimido[1,2-a]pyrimidin-4-one;
(S)-9-[2-phenyl-2-hydroxyethyl]-2-pyridin-4-yl-6,7,8,9-tetrahydro-4H-pyrimido[1,2-a]pyrimidin-4-one;
9-[3-(4-fluorophenyl)-3-hydroxypropyl]-2-pyridin-4-yl-6,7,8,9-tetrahydro-4H-pyrimido[1,2-a]pyrimidin-4-one;
9-[1-methyl-2-oxo-2-phenyl-ethyl]-2-pyridin-4-yl-6,7,8,9-tetrahydro-4H-pyrimido[1,2-a]pyrimidin-4-one;
9-[1-methyl-2-hydroxy-2-phenyl-ethyl]-2-pyridin-4-yl-6,7,8,9-tetrahydro-4H-pyrimido[1,2-a]pyrimidin-4-one;
9-[2-(4-methylphenyl)-2-oxo-ethyl]-2-pyridin-4-yl-6,7,8,9-tetrahydro-4H-pyrimido[1,2-a]pyrimidin-4-one;
9-[2-(4-chlorophenyl)-2-oxo-ethyl]-2-pyridin-4-yl-6,7,8,9-tetrahydro-4H-pyrimido[1,2-a]pyrimidin-4-one;
9-[2-(4-fluorophenyl)-2-oxo-ethyl]-2-pyridin-4-yl-6,7,8,9-tetrahydro-4H-pyrimido[1,2-a]pyrimidin-4-one;
9-[2-(4-phenylphenyl)-2-oxo-ethyl]-2-pyridin-4-yl-6,7,8,9-tetrahydro-4H-pyrimido[1,2-a]pyrimidin-4-one;
9-[2-(3-methoxyphenyl)-2-oxo-ethyl]-2-pyridin-4-yl-6,7,8,9-tetrahydro-4H-pyrimido[1,2-a]pyrimidin-4-one;
9-[2-(2-naphthyl)-2-oxo-ethyl]-2-pyridin-4-yl-6,7,8,9-tetrahydro-4H-pyrimido[1,2-a]pyrimidin-4-one;
9-[2-(5,5,8,8-tetramethyl-5,6,7,8-tetrahydronapht-2-yl)-2-oxo-ethyl]-2-pyridin-4-yl-6,7,8,9-tetrahydro-4H-pyrimido[1,2-a]pyrimidin-4-one;
9-[2-(3-methoxy-4,5-methylendioxyphenyl)-2-oxo-1-methylethyl]-2-pyridin-4-yl-6,7,8,9-tetrahydro-4H-pyrimido[1,2-a]pyrimidin-4-one;
9-[2-(4-methylphenyl)-2-hydroxy-ethyl]-2-pyridin-4-yl-6,7,8,9-tetrahydro-4H-pyrimido[1,2-a]pyrimidin-4-one;
9-[2-(1,1,4,4,-tetramethyl-1,2,3,4-tetrahydronapht-6-yl)-2-hydroxy-ethyl]-2-pyridin-4-yl-6,7,8,9-tetrahydro-4H-pyrimido[1,2-a]pyrimidin-4-one;
9-[2-(phenylamino)-2-oxo-ethyl]-2-pyridin-4-yl-6,7,8,9-tetrahydro-4H-pyrimido[1,2-a]pyrimidin-4-one;
9-[2-(3-chlorophenyl)-2-oxo-ethyl]-2-pyridin-4-yl-6,7,8,9-tetrahydro-4H-pyrimido[1,2-a]pyrimidin-4-one;
9-[2-(3-chlorophenyl)-2-hydroxy-ethyl]-2-pyridin-4-yl-6,7,8,9-tetrahydro-4H-pyrimido[1,2-a]pyrimidin-4-one;
9-[2-(3-fluorophenyl)-2-oxo-ethyl]-2-pyridin-4-yl-6,7,8,9-tetrahydro-4H-pyrimido[1,2-a]pyrimidin-4-one; and
9-[2-(3-fluorophenyl)-2-hydroxy-ethyl]-2-pyridin-4-yl-6,7,8,9-tetrahydro-4H-pyrimido[1,2-a]pyrimidin-4-one;
or a pharmaceutically acceptable salt thereof.

5. The method according to claim 1, wherein said compound of formula I is selected from the group consisting of:

1-[2-(1H-Indol-3-yl)ethyl]-7-pyridin-4-yl-2,3-dihydroimidazo[1,2-a]pyrimidin-5(1H)-one,
1-[3-(phenyl)propyl]-7-pyridin-4-yl-2,3-dihydroimidazo[1,2-a]pyrimidin-5 (1H)-one,
1-[3-(1H-indol-3-yl)propyl]-7-pyridin-4-yl-2,3-dihydroimidazo[1,2-a]pyrimidin-5(1H)-one,
1-[2-(phenyl)ethyl]-7-pyridin-4-yl-2,3-dihydroimidazo[1,2-a]pyrimidin-5 (1H)-one,
1-[3-(2-methylphenyl)propyl]-7-pyridin-4-yl-2,3-dihydroimidazo[1,2-a]pyrimidin-5(1H)-one,
1-[3-(2-methoxyphenyl)propyl]-7-pyridin-4-yl-2,3-dihydroimidazo[1,2-a]pyrimidin-5(1H)-one,
1-(4-phenylbutyl)-7-pyridin-4-yl-2,3-dihydroimidazo[1,2-a]pyrimidin-5 (1H)-one,
1-[3-(2-chlorophenyl)propyl]-7-pyridin-4-yl-2,3-dihydroimidazo[1,2-a]pyrimidin-5(1H)-one,
1-[3-(2,5-dimethoxyphenyl)propyl]-7-pyridin-4-yl-2,3-dihydroimidazo[1,2-a]pyrimidin-5(1H)-one,
1-[3-(4-methylphenyl)propyl]-7-pyridin-4-yl-2,3-dihydroimidazo[1,2-a]pyrimidin-5(1H)-one,
1-[3-(3-methoxyphenyl)propyl]-7-pyridin-4-yl-2,3-dihydroimidazo[1,2-a]pyrimidin-5(1H)-one,
1-[3-(3,4,5-trimethoxyphenyl)propyl]-7-pyridin-4-yl-2,3-dihydroimidazo[1,2-a]pyrimidin-5(1H)-one,
1-[2-(4-fluorophenoxy)ethyl]-7-pyridin-4-yl-2,3-dihydroimidazo[1,2-a]pyrimidin-5(1H)-one,
1-[2-(4-chlorophenoxy)ethyl]-7-pyridin-4-yl-2,3-dihydroimidazo[1,2-a]pyrimidin-5(1H)-one,
1-[3-(2,4-dichlorophenyl)propyl]-7-pyridin-4-yl-2,3-dihydroimidazo[1,2-a]pyrimidin-5(1H)-one,
1-[2-(phenylthio)ethyl]-7-pyridin-4-yl-2,3-dihydroimidazo[1,2-a]pyrimidin-5(1H)-one,
1-(3-phenylpropanoyl)-7-pyridin-4-yl-2,3-dihydroimidazo[1,2-a]pyrimidin-5(1H)-one,
1-[3-(4-fluorophenyl)propyl]-7-pyridin-4-yl-2,3-dihydroimidazo[1,2-a]pyrimidin-5(1H)-one,
1-[3-(3,4-difluorophenyl)propyl]-7-pyridin-4-yl-2,3-dihydroimidazo[1,2-a]pyrimidin-5(1H)-one,
1-(2-cyclohexylethyl)-7-pyridin-4-yl-2,3-dihydroimidazo[1,2-a]pyrimidin-5 (1H)-one,
1-(3,3-dimethylbutyl)-7-pyridin-4-yl-2,3-dihydroimidazo[1,2-a]pyrimidin-5 (1H)-one,
1-(2-phenyl-2-oxo-ethyl)-7-pyridin-4-yl-2,3-dihydroimidazo[1,2-a]pyrimidin-5(1H)-one,
(S)-1-(4,4,4-trifluoro-3-hydroxybutyl)-7-pyridin-4-yl-2,3-dihydroimidazo[1,2-a]pyrimidin-5(1H)-one,
1-(4,4,4-trifluoro-but-2-en-1-yl)-7-pyridin-4-yl-2,3-dihydroimidazo[1,2-a]pyrimidin-5(1H)-one,
1-[3-(4-trifluoromethylphenyl)propyl]-7-pyridin-4-yl-2,3-dihydroimidazo[1,2-a]pyrimidin-5(1H)-one,
(R)-1-(4,4,4-trifluoro-3-hydroxybutyl)-7-pyridin-4-yl-2,3-dihydroimidazo[1,2-a]pyrimidin-5(1H)-one,
1-[3-(2-fluorophenyl)propyl]-7-pyridin-4-yl-2,3-dihydroimidazo[1,2-a]pyrimidin-5(1H)-one,
1-[2-(2,5-dimethoxy-phenyl)ethyl]-7-pyridin-4-yl-2,3-dihydroimidazo[1,2-a]pyrimidin-5(1H)-one,
1-[2-(phenylsulfonyl)ethyl]-7-pyridin-4-yl-2,3-dihydroimidazo[1,2-a]pyrimidin-5(1H)-one,
1-(4,4,4-trifluorobutyl)-7-pyridin-4-yl-2,3-dihydroimidazo[1,2-a]pyrimidin-5(1H)-one,
1-[3-(pyridin-3-yl)propyl]-7-pyridin-4-yl-2,3-dihydroimidazo[1,2-a]pyrimidin-5(1H)-one,
1-[2-(2-methoxy)ethyl]-7-pyridin-4-yl-2,3-dihydroimidazo[1,2-a]pyrimidin-5(1H)-one,
1-[2-(4-chloro-phenyl)-2-oxo-ethyl]-7-pyridin-4-yl-2,3-dihydroimidazo[1,2-a]pyrimidin-5(1H)-one,
1-[2-(napht-2-yl)-2-oxo-ethyl]-7-pyridin-4-yl-2,3-dihydroimidazo[1,2-a]pyrimidin-5(1H)-one,
1-[2-(3-methoxy-4,5-methylendioxy-phenyl)-2-oxo-1-methyl-ethyl]-7-pyridin-4-yl-2,3-dihydroimidazo[1,2-a]pyrimidin-5 (1H)-one,
1-[2-(4-phenyl-phenyl)-2-oxo-ethyl]-7-pyridin-4-yl-2,3-dihydroimidazo[1,2-a]pyrimidin-5(1H)-one,
1-[2-(4-methylphenyl)-2-oxo-ethyl]-7-pyridin-4-yl-2,3-dihydroimidazo[1,2-a]pyrimidin-5(1H)-one,
1-[2-(5,5,8,8-tetramethyl-5,6,7,8-tetrahydronapht-2-yl)-2-oxo-ethyl]-7-pyridin-4-yl-2,3-dihydroimidazo[1,2-a]pyrimidin-5(1H)-one,
1-[2-(4-fluorophenyl)-2-oxo-ethyl]-7-pyridin-4-yl-2,3-dihydroimidazo[1,2-a]pyrimidin-5(1H)-one, and
1-[2-(3-methoxyphenyl)-2-oxo-ethyl]-7-pyridin-4-yl-2,3-dihydroimidazo[1,2-a]pyrimidin-5(1H)-one;
or a pharmaceutically acceptable salt thereof.

* * * * *